US008221738B2

(12) United States Patent
Zsebo

(10) Patent No.: US 8,221,738 B2
(45) Date of Patent: Jul. 17, 2012

(54) METHOD FOR ENHANCED UPTAKE OF VIRAL VECTORS IN THE MYOCARDIUM

(75) Inventor: Krisztina Maria Zsebo, Del Mar, CA (US)

(73) Assignee: Celladon Corporation, La Jolla, CA (US)

( * ) Notice: Subject to any disclaimer, the term of this patent is extended or adjusted under 35 U.S.C. 154(b) by 489 days.

(21) Appl. No.: 12/260,953

(22) Filed: Oct. 29, 2008

(65) Prior Publication Data

US 2009/0209631 A1 Aug. 20, 2009

Related U.S. Application Data

(60) Provisional application No. 61/029,881, filed on Feb. 19, 2008.

(51) Int. Cl.
*A01N 63/00* (2006.01)
*C12N 5/00* (2006.01)

(52) U.S. Cl. ........ 424/93.1; 977/913; 435/325; 530/841

(58) Field of Classification Search .................. None
See application file for complete search history.

(56) References Cited

U.S. PATENT DOCUMENTS

| | | |
|---|---|---|
| 4,797,368 A | 1/1989 | Carter et al. |
| 5,139,941 A | 8/1992 | Muzyczka et al. |
| 5,328,470 A | 7/1994 | Nabel et al. |
| 5,478,745 A | 12/1995 | Samulski et al. |
| 5,658,785 A | 8/1997 | Johnson |
| 5,661,133 A | 8/1997 | Leiden et al. |
| 5,698,531 A | 12/1997 | Nabel et al. |
| 5,707,969 A | 1/1998 | Nabel et al. |
| 5,773,289 A | 6/1998 | Samulski et al. |
| 5,792,453 A | 8/1998 | Hammond et al. |
| 5,858,351 A | 1/1999 | Podsakoff et al. |
| 5,863,904 A | 1/1999 | Nabel et al. |
| 6,057,300 A | 5/2000 | Nabel et al. |
| 6,090,618 A | 7/2000 | Parmacek et al. |
| 6,100,242 A | 8/2000 | Hammond et al. |
| 6,114,311 A | 9/2000 | Parmacek et al. |
| 6,162,796 A | 12/2000 | Kaplitt et al. |
| 6,165,781 A | 12/2000 | Carter et al. |
| 6,174,871 B1 | 1/2001 | Hammond et al. |
| 6,177,272 B1 | 1/2001 | Nabel et al. |
| 6,203,991 B1 | 3/2001 | Nabel et al. |
| 6,218,372 B1 | 4/2001 | Nabel et al. |
| 6,268,213 B1 | 7/2001 | Samulski et al. |
| 6,284,743 B1 | 9/2001 | Parmacek et al. |
| 6,291,211 B1 | 9/2001 | Parmacek et al. |
| 6,297,220 B1 | 10/2001 | Leiden et al. |
| 6,297,221 B1 | 10/2001 | Parmacek et al. |
| 6,306,830 B1 | 10/2001 | Hammond et al. |
| 6,316,419 B1 | 11/2001 | Leiden et al. |
| 6,323,184 B1 | 11/2001 | Zalewski et al. |
| 6,325,998 B1 | 12/2001 | Podsakoff et al. |
| 6,331,527 B1 | 12/2001 | Parmacek et al. |
| 6,391,858 B2 | 5/2002 | Podsakoff et al. |
| 6,410,300 B1 | 6/2002 | Samulski et al. |
| 6,436,907 B1 | 8/2002 | Leiden et al. |
| 6,605,274 B1 | 8/2003 | Dillmann et al. |
| 6,610,290 B2 | 8/2003 | Podsakoff et al. |
| 6,670,176 B1 | 12/2003 | Samulski et al. |
| 6,703,237 B2 | 3/2004 | Samulski et al. |
| 6,752,987 B1 | 6/2004 | Hammond et al. |
| 6,759,237 B1 | 7/2004 | Wilson et al. |
| 6,770,473 B1 | 8/2004 | Nabel et al. |
| 6,855,701 B2 | 2/2005 | Lawrence, III et al. |
| 6,867,196 B1 | 3/2005 | Wolff et al. |
| 6,958,147 B1 | 10/2005 | Alitalo et al. |
| 6,992,070 B2 | 1/2006 | Donahue et al. |
| 7,034,008 B2 | 4/2006 | Donahue et al. |
| 7,078,387 B1 | 7/2006 | Leiden et al. |
| 7,105,345 B2 | 9/2006 | Wilson et al. |
| 7,172,893 B2 | 2/2007 | Rabinowitz et al. |
| 7,186,552 B2 | 3/2007 | Wilson et al. |
| 7,201,898 B2 | 4/2007 | Monahan et al. |
| 7,229,823 B2 | 6/2007 | Samulski et al. |

(Continued)

FOREIGN PATENT DOCUMENTS

AU 200018111 B2 5/2000

(Continued)

OTHER PUBLICATIONS

Kizana et al. Heart, Lung and Circulation 2007;16:180-184.*
U.S. Appl. No. 11/778,900, filed Jul. 17, 2007, Zsebo, K.
Andrews, et al., "The MKK6-p38 MAPK Pathway Prolongs the Cardiac Contractile Calcium Transient, Downregulates SERCA2, and Activates NF-AT," *Cardiovascular Research* (2003) 59: 46-56.
Anversa et al., "Ventricular myocytes are not terminally differentiated in the adult mammalian heart," Circ Res. (1998) 83(1):1-14.
Berg, et al., *Biochemistry*, 6th Ed., W.H. Freeman and Company (2006).
Byrne et al., "Recirculating cardiac delivery of AAV2/1SERCA2a improves myocardial function in an experimental model of heart failure in large animals," Gene Ther. (2008) 15(23):1550-1557. Epub Jul. 24, 2008.

(Continued)

*Primary Examiner* — Doug Schultz
(74) *Attorney, Agent, or Firm* — Knobbe, Martens, Olson & Bear

(57) ABSTRACT

The present invention relates to improved therapies for the treatment of heart disease, particularly the improved delivery of therapeutic agents to heart tissue by direct infusion into the coronary circulation. A preferred embodiment of the invention is a method of treating or preventing a cardiovascular disease by transfecting cardiac cells of a large mammal, the method comprising, identifying a mammal in need of treatment or prevention of heart disease, supplying NO to the coronary circulation prior to, and/or during the infusion of a therapeutic polynucleotide into a blood vessel of the coronary circulation in vivo, where the therapeutic polynucleotide is infused into the blood vessel over a period of at least about three minutes, where the coronary circulation is not isolated or substantially isolated from the systemic circulation of the mammal; and where the therapeutic polynucleotide transfects cardiac cells of the animal resulting in the treatment or prevention of the heart disease.

23 Claims, 4 Drawing Sheets

U.S. PATENT DOCUMENTS

| | | | |
|---|---|---|---|
| 7,291,604 | B2 | 11/2007 | Hajjar et al. |
| 7,745,416 | B2 | 6/2010 | Dillman et al. |
| 7,781,415 | B2 | 8/2010 | Herweijer et al. |
| 2002/0106381 | A1 | 8/2002 | High |
| 2002/0155101 | A1 | 10/2002 | Donahue et al. |
| 2002/0159978 | A1 | 10/2002 | Allen |
| 2003/0148968 | A1 | 8/2003 | Hammond et al. |
| 2003/0211080 | A1 | 11/2003 | Dillmann et al. |
| 2004/0009940 | A1 | 1/2004 | Coleman et al. |
| 2004/0057931 | A1 | 3/2004 | Wilson et al. |
| 2004/0106954 | A1 | 6/2004 | Whitehurst et al. |
| 2004/0132190 | A1 | 7/2004 | Dillmann et al. |
| 2004/0157790 | A1 | 8/2004 | Herweijer et al. |
| 2004/0214182 | A1 | 10/2004 | Sharma et al. |
| 2004/0254134 | A1 | 12/2004 | Marban et al. |
| 2004/0266716 | A1 | 12/2004 | Donahue et al. |
| 2004/0266717 | A1 | 12/2004 | Donahue et al. |
| 2005/0095227 | A1 | 5/2005 | Rosenzweig et al. |
| 2005/0107323 | A1 | 5/2005 | Donahue et al. |
| 2005/0112101 | A1 | 5/2005 | Hajjar et al. |
| 2005/0192637 | A1 | 9/2005 | Girouard et al. |
| 2005/0222075 | A1 | 10/2005 | Herweijer et al. |
| 2005/0250721 | A1 | 11/2005 | Hammond et al. |
| 2006/0148742 | A1 | 7/2006 | Kaye et al. |
| 2006/0204479 | A1 | 9/2006 | Wilson et al. |
| 2006/0251626 | A1 | 11/2006 | Leiden et al. |
| 2006/0286072 | A1* | 12/2006 | Giordano et al. ............ 424/93.2 |
| 2008/0008684 | A1 | 1/2008 | Wilson et al. |
| 2008/0050343 | A1 | 2/2008 | Wilson et al. |
| 2008/0050345 | A1 | 2/2008 | Wilson et al. |
| 2008/0076730 | A1 | 3/2008 | Zsebo |
| 2008/0124379 | A1 | 5/2008 | Kaemmerer et al. |
| 2009/0209631 | A1 | 8/2009 | Zsebo |
| 2009/0239940 | A1 | 9/2009 | Del Monte et al. |

FOREIGN PATENT DOCUMENTS

| | | |
|---|---|---|
| EP | 0 644 944 B1 | 11/2001 |
| EP | 1232759 A1 | 8/2002 |
| EP | 1374909 A2 | 1/2004 |
| EP | 1374909 A3 | 1/2004 |
| EP | 1126870 B1 | 9/2004 |
| EP | 1695719 A1 | 8/2006 |
| EP | 1 127 150 B1 | 5/2007 |
| WO | WO 93/24641 A2 | 12/1993 |
| WO | WO 93/24641 A3 | 12/1993 |
| WO | WO 96/26742 | 9/1996 |
| WO | WO 96/32139 | 10/1996 |
| WO | WO 96/40195 | 12/1996 |
| WO | WO 98/10085 A2 | 3/1998 |
| WO | WO 98/10085 A3 | 3/1998 |
| WO | WO 98/50079 A2 | 11/1998 |
| WO | WO 98/50079 A3 | 11/1998 |
| WO | WO 99/40945 A2 | 8/1999 |
| WO | WO 99/40945 A3 | 8/1999 |
| WO | WO 00/24412 A2 | 5/2000 |
| WO | WO 00/24412 A3 | 5/2000 |
| WO | WO 00/25804 A3 | 5/2000 |
| WO | WO 00/28061 A2 | 5/2000 |
| WO | WO 00/28061 A3 | 5/2000 |
| WO | WO 00/38518 A1 | 7/2000 |
| WO | WO 01/34208 | 5/2001 |
| WO | WO 01/48164 A2 | 7/2001 |
| WO | WO 01/48164 A3 | 7/2001 |
| WO | WO 02/19966 A2 | 3/2002 |
| WO | WO 02/19966 A3 | 3/2002 |
| WO | WO 02/22177 A2 | 3/2002 |
| WO | WO 02/22177 A3 | 3/2002 |
| WO | WO 02/089856 A1 | 11/2002 |
| WO | WO 2004/062618 A2 | 7/2004 |
| WO | WO 2004/062618 A3 | 7/2004 |
| WO | WO 2005/003323 A2 | 1/2005 |
| WO | WO 2005/003323 A3 | 1/2005 |
| WO | WO 2005/060746 A1 | 7/2005 |
| WO | WO 2008/013692 A2 | 1/2008 |
| WO | WO 2008/013692 A3 | 1/2008 |
| WO | WO 2009/105135 A1 | 8/2009 |

OTHER PUBLICATIONS

Calcedo et al., "Worldwide epidemiology of neutralizing antibodies to adeno-associated viruses," J Infect Dis. (2009) 199(3):381-390.

Carter, "Adeno-associated virus vectors in clinical trials," Hum Gene Ther. (2005) 16(5):541-550.

Carter et al., AAV vectors for gene delivery, in gene and cell therapy: therapeutic mechanisms and strategies, $2^{nd}$ ed., N. Templeton, Editor. (2004) Marcel Dekker: New York, 55-101.

Clark et al., "Highly Purified Recombinant Adeno-associated Virus Vectors are Biologically Active and Free of Detectable Helper and Wild-type Virus," Human Gene Therapy (1999) 10: 1031-1039.

Crameri, et al., "DNA Shuffling of a Family of Genes from Diverse Species Accelerates Directed Evolution," Nature (1998) 391:288-291.

Davia et al., "SERCA2A overexpression decreases the incidence of aftercontractions in adult rabbit ventricular myocytes," J Mol Cell Cardiol. (2001) 33(5):1005-1015.

Del Monte et al., "Restoration of contractile function in isolated cardiomyocytes from failing human hearts by gene transfer of SERCA2a.," Circulation (1999) 100:2308-2311.

Del Monte et al., "Improvement in survival and cardiac metabolism after gene transfer of sarcoplasmic reticulum Ca(2+)-ATPase in a rat model of heart failure," Circulation. (2001) 104(12):1424-1429.

Del Monte et al., "Targeting calcium cycling proteins in heart failure through gene transfer," J Physiol. (2003) 546(Pt 1):49-61.

Donahue, et al., "Ultrarapid, highly efficient viral gene transfer to the heart," Proc. Natl. Acad. Sci. USA (1997) 94:4664-4668.

Eppler et al., "Unique Kinetics and Hemodynamics of Vascular Endothelial Growth Factor (rhVEGF) Following Intracoronary and Intravenous Infusion in Humans," JACC, ACCIS2000 (Angiography and Interventional Cardiology) (2000) 73A-74A.

Flotte, et al., "Stable In Vivo Expression of the Cystic Fibrosis Transmembrane Conductance Regulator with an Adeno-associated Virus Vector," Proc. Natl. Acad. Sci. USA (1993) 90:10613-10617.

Gao, et al., "Novel Adeno-associated Viruses from Rhesus Monkeys as Vectors for Human Gene Therapy," Proc. Natl. Acad. Sci. USA (2002) 99(18): 11854-11859.

Gruchala et al., "Gene Transfer into Rabbit Arteries with Adeno-associated Virus and Adenovirus Vectors," J. Gene Med. (2004) 6(5):545-54.

Gwathmey et al., "Abnormal intracellular calcium handling in myocardium from patients with end-stage heart failure," Circ Res. (1987) 61(1):70-76.

Gwathmey et al., "Relation between steady-state force and intracellular [Ca2+] in intact human myocardium. Index of myofibrillar responsiveness to Ca2+," Circulation (1990) 82(4):1266-1278.

Gwathmey et al., "Role of intracellular calcium handling in force-interval relationships of human ventricular myocardium," J Clin Invest. (1990) 85(5):1599-1613.

Hajjar et al., "Physiological effects of adenoviral gene transfer of sarcoplasmic reticulum calcium ATPase in isolated rat myocytes," Circulation. (1997) 95(2):423-429.

Hajjar et al., "Adenoviral gene transfer of phospholamban in isolated rat cardiomyocytes. Rescue effects by concomitant gene transfer of sarcoplasmic reticulum Ca(2+)-ATPase," Circ Res. (1997) 81(2):145-153.

Hajjar et al., "Modulation of Ventricular Function through Gene Transfer in Vivo," Proc Natl. Acad. Sci. USA (1998) 95(9):5251-6.

Hajjar, et al., "Design of a Phase 1/2 Trial of Intracoronary Administration of AAV1/SERCA2a in Patients with Heart Failure," Journal of Cardiac Failure (2008) 14(5): 355-67.

Hasenfuss et al., "Relation between myocardial function and expression of sarcoplasmic reticulum Ca(2+)-ATPase in failing and nonfailing human myocardium," Circ Res. (1994) 75(3):434-442.

Hauck, et al., "Generation and Characterization of Chimeric Recombinant AAV Vectors," Mol. Ther. (2003) 7(3): 419-425.

Hayase, et al., "Catheter-based Antegrade Intracoronary Viral Gene Delivery with Coronary Venous Blockade," Am. J. Physiol. Heart Circ. Physiol. (2005) 288(6):H2995-3000.

Jaski et al., "Calcium upregulation by percutaneous administration of gene therapy in cardiac disease (CUPID Trial), a first-in-human phase 1/2 clinical trial," J Card Fail. (2009) 15(3):171-181.

Jost et al., "Standardization of Coronary Vasomotor Tone with Intracoronary Nitroglycerin," Am. J. Cardiol. (1996) 78(1):120-3.

Kaplitt, et al., "Long-term Gene Transfer in Porcine Myocardium After Coronary Infusion of an Adeno-associated Virus Vector," *Ann. Thorac. Surg.* (1996) 62(6):1669-1676.

Kaspar et al., "Myocardial Gene Transfer and Long-term Expression Following Intracoronary Delivery of Adeno-associated Virus," *J. Gene Med.* (2005) 7(3):316-324.

Katz, et al., "Cardiac Gene Therapy: Optimization of Gene Delivery Techniques in Vivo," Hum Gene Ther. (2009) [Epub ahead of print] doi:10.1089/hum.2009.164.

Kawase et al., "Reversal of cardiac dysfunction after long-term expression of SERCA2a by gene transfer in a pre-clinical model of heart failure," J Am Coll Cardiol. (2008) 51(11):1112-1119.

Kawase et al., "The cardiac sarcoplasmic/endoplasmic reticulum calcium ATPase: a potent target for cardiovascular diseases," Nat Clin Pract Cardiovasc Med. (2008) 5(9):554-565. Epub Jul. 29, 2008.

Li et al., "KDR (VEGF receptor 2) is the Major Mediator for the Hypotensive Effect of VEGF," American Heart Association, *Hypertension* (2002) 39:1095-1100.

Li, et al., "Protection from the Toxicity of Diisopropylfluorophosphate by Adeno-associated Virus Expressing Acetylcholinesterase," *Toxicol. Appl. Pharmacol.* (2006) 214(2):152-165.

Li, et al., "Engineering and Selection of Shuffled AAV Genomes: A New Strategy for Producing Targeted Biological Nanoparticles," *Molecular Therapy* (2008) 16(7): 1252-1260.

Lincoff, et al., "Local drug delivery for the prevention of restenosis. Fact, fancy, and future," *Circulation* (1994) 90(4):2070-2084.

Lipskaia et al., "Treatment of heart failure by calcium cycling gene therapy," Future Cardiol. (2007) 3(4):413-423.

Liu, et al., "Herne Oxygenase-1 (HO-1) Inhibits Postmyocardial Infarct Remodeling and Restores Ventricular Function," *FASEB J.* (2006) 20(2):207-16.

Logeart et al., "Percutaneous intracoronary delivery of SERCA gene increases myocardial function: a tissue Doppler imaging echocardiographic study," *Am J Physiol Heart Circ Physiol.* (2006) 1(4):H1773-9. Epub Jun. 9, 2006.

Lompré et al., "Ca2+ cycling and new therapeutic approaches for heart failure," Circulation (2010) 121(6):822-830. Epub Feb. 1, 2010.

Maheshri, N et al., "Directed Evolution of Adeno-associated Virus Yields Enhanced Gene Delivery Vectors," *Nat Biotechnol.* (2006) 24:198-204.

Mazur et al., "Coronary Restenosis and Gene Therapy," Texas Heart Institute Journal, Molecular and Cellular Cardiology (1994) 21(1): 104-111.

McAlpine, W., *Heart and Coronary Arteries: An Anatomical Atlas for Clinical Diagnosis, Radiological Investigation, and Surgical Treatment*, Springer Verlag, New York (1975).

Megson, et al., "Nitric Oxide Donor Drugs: Current Status and Future Trends," *Expert. Opin. Investig. Drugs* (2002) 11(5):587-601.

Meyer et al., "Alterations of sarcoplasmic reticulum proteins in failing human dilated cardiomyopathy," Circulation. (1995) 92(4):778-784.

Miyamoto, et al. "Adenoviral Gene Transfer of SERCA2a Improves Left-ventricular Function in Aortic-banded Rats in Transition to Heart Failure," *Proc. Natl. Acad. Sci. USA* (2000) 97(2):793-798.

Moore, et al., "Modeling DNA Mutation and Recombination for Directed Evolution Experiments," *J. Theor. Biol.* (2000) 205: 483-503.

Murata, et al. "Creation of a Genetic Calcium Channel Blocker by Targeted Gem Gene Transfer in the Heart," *Circulation Research* (2004) 398-405.

Nykanen, et al., "Common Protective and Diverse Smooth Muscle Cell Effects of AAV-mediated Angiopoietin-1 and -2 Expression in Rat Cardiac Allograft Vasculopathy," *Circ. Res.* (2006) 98(11):1373-80.

Roth, et al., "Nitroprusside Increases Gene Transfer Associated with Intracoronary Delivery of Adenovirus," *Human Gene Therapy* (2004) 15(10):989-994.

Sasano, et al., "Targeted High-Efficiency, Homogenous Myocardial Gene Transfer," *J. Mol. Cell. Cardiol.* (2007) 42(5):954-961.

Schmidt et al., "Contribution of abnormal sarcoplasmic reticulum atpase activity to systolic and diastolic dysfunction in human heart failure," J Mol Cell Cardiol. (1998) 30(10):1929-1937.

Schmidt et al., "Human heart failure: cAMP stimulation of SR Ca(2+)-ATPase activity and phosphorylation level of phospholamban," Am J Physiol. (1999) 277(2 pt 2):H474-80.

Schnepp et al., "Characterization of adeno-associated virus genomes isolated from human tissues," J Virol. (2005) 79(23):14793-14803.

Song, et al., "Effect of DNA-dependent Protein Kinase on the Molecular Fate of the rAAV2 Genome in Skeletal Muscle," *Proc. Natl. Acad. Sci.* (2001) 98(7):4084-4088.

Stemmer, W., "Rapid Evolution of a Protein in Vitro by DNA Shuffling," *Nature* (1994) 370:389-391.

Vlodaver, et al., *Coronary Heart Disease: Clinical, Angiographic, and Pathologic Profiles*, Spinger-Verlag, New York (1976).

Walsh, et al., "Phenotypic Correction of Fanconi Anemia in Human Hematopoietic Cells with a Recombinant Adeno-associated Virus Vector," *J. Clin. Invest.* (1994) 94:1440-1448.

Wilensky, et al., "Methods and Devices for Local Drug Delivery in Coronary and Peripheral Arteries," *TCM* (1993) 3(5):163:170.

Zhu, et al- "Sustained Whole-body Functional Rescue in Congestive Heart Failure and Muscular Dystrophy Hamsters by Systemic Gene Transfer," *Circulation* (2005) 112(17):2650-9.

International Search Report and Written Opinion dated Mar. 10, 2008 for International Application No. PCT/US2007/016129, filed Jul. 16, 2007.

International Preliminary Report on Patentability dated Aug. 27, 2008 for International Application No. PCT/US2007/016129, filed Jul. 16, 2007.

International Search Report and Written Opinion of the International Searching Authority dated Feb. 20, 2009 for International Application No. PCT/US2008/081634, filed Oct. 29, 2008.

International Preliminary Report on Patentability dated Apr. 14, 2010 for International Application No. PCT/US2008/081634, filed Oct. 29, 2008.

Alexander et al., "DNA-damaging agents greatly increase the transduction of nondividing cells by adeno-associated virus vectors", J. Virol. (1994) 68(12):8282-8287.

Ding et al., "A minimally invasive approach for efficient gene delivery to rodent hearts", Gene Ther. (2004) 11(3):260-265.

Donahue et al., "Acceleration of widespread adenoviral gene transfer to intact rabbit hearts by coronary perfusion with low calcium and serotonin", Gene Ther. (1998) 5(5):630-634.

Grünenfelder et al., "Upregulation of Bcl-2 through caspase-3 inhibition ameliorates ischemia/reperfusion injury in rat cardiac allografts", Circulation. Sep. 18, 2001;104(12 Suppl 1):I202-I206.

Ikeda et al., "Restoration of deficient membrane proteins in the cardiomyopathic hamster by in vivo cardiac gene transfer", Circulation (2002) 105(4):502-508.

Jessup et al., "Calcium Upregulation by Percutaneous Administration of Gene Therapy in Cardiac Disease (CUPID): a phase 2 trial of intracoronary gene therapy of sarcoplasmic reticulum Ca2+-ATPase in patients with advanced heart failure", Circulation (2011) 124(3):304-313. Epub Jun. 27, 2011.

Karakikes et al., "Concomitant Intravenous Nitroglycerin With Intracoronary Delivery of AAV1.SERCA2a Enhances Gene Transfer in Porcine Hearts", Mol Ther. (Jan. 3, 2012) doi: 10.1038/mt.2011.268. [Epub ahead of print].

Kawamoto et al., "Widespread and early myocardial gene expression by adeno-associated virus vector type 6 with a beta-actin hybrid promoter." Mol. Ther. (2005) 11(6):980-985.

Kawase, et.al., "The long-term effects of SERCA2a overexpression in large animal model of heart failure", Mol. Ther. (2005) 11(S20).

Logeart et al., "Highly efficient adenovirus-mediated gene transfer to cardiac myocytes after single-pass coronary delivery", Hum Gene Ther. (2000) 11(7):1015-1022.

Logeart et al., "How to optimize in vivo gene transfer to cardiac myocytes: mechanical or pharmacological procedures?" Hum Gene Ther. (2001) 12(13):1601-1610.

Renner et al., "Heterotopic rat heart transplantation: severe loss of glutathione in 8-hour ischemic hearts", J Heart Lung Transplant (2004) 23(9):1093-1102.

Wang et al., "DNA/dendrimer complexes mediate gene transfer into murine cardiac transplants ex vivo", Mol Ther (2000) 2:602-608.

Wheeler et al., "Chronic ethanol increases adeno-associated viral transgene expression in rat liver via oxidant and NFkappaB-dependent mechanisms", Hepatology (2000) 32(5):1050-1059.

Wright et al., "In vivo myocardial gene transfer: optimization and evaluation of intracoronary gene delivery in vivo", Gene Ther. (2001) 8(24):1833-1839.

Office Action dated Feb. 2, 2009 for U.S. Appl. No. 11/778,900, filed Jul. 17, 2007.

Office Action dated Oct. 15, 2009 for U.S. Appl. No. 11/778,900, filed Jul. 17, 2007.

* cited by examiner

METHOD FOR ENHANCED UPTAKE OF VIRAL VECTORS IN THE MYOCARDIUM

CROSS-REFERENCE TO RELATED APPLICATIONS

This application is a non-provisional of U.S. Provisional Patent Application Ser. No. 61/029,881, filed Feb. 19, 2008, from which priority is claimed under 35 USC section 119(e)(1), and which application is incorporated herein by reference in its entirety.

BACKGROUND OF THE INVENTION

1. Field of the Invention

The present invention relates to gene therapies for the treatment of heart diseases, particularly the enhanced delivery of polynucleotides to heart tissue.

2. Description of the Related Art

Heart disease is a major public health issue of very high prevalence, especially in the Western world. Cardiac conditions include coronary artery disease, ischemic heart disease, angina, heart failure, valvular heart disease, cardiac arrhythmias and cardiac inflammation (myocarditis) to name a few. Coronary artery disease and heart failure are possibly the most serious and prevalent, together being a leading cause of death in the Western world. The impact of acute myocardial infarction and congestive heart failure and their sequelae on the quality of life of patients and the cost of health care drives the search for new therapies.

Heart failure (HF) is a serious condition in which the heart loses its ability to pump blood efficiently. Data from the National Heart, Lung and Blood Institute, suggests about 5 million people in the United States alone have heart failure, and another 550,000 new cases are diagnosed each year. HF contributes to or causes about 300,000 deaths annually. The disease is most common in people aged 65 or older, women and African Americans. The most common symptoms of heart failure are shortness of breath, feeling tired, and swelling in the ankles, feet, legs, and sometimes the abdomen. There is no cure for congestive heart failure, and a clear need exists in the art for effective therapies.

One method of treating heart disease, such as HF, which has begun to receive more attention is gene therapy, wherein a polynucleotide is delivered to the cardiac tissue, typically in a viral vector. Numerous means of delivering viral vector to the heart have been attempted, including direct injection into the heart muscle (Liu et al., FASEB J. 2006; 20(2):207-16; Li et al. Toxicol. Appl. Pharmacol. Jan. 25, 2006 (electronic publication); Zhu et al., Circulation. 2005; 112(17):2650-9), intracoronary delivery (Nykanen et al., Circ. Res. 2006; 98(11):1373-80; Kaspar et al., J. Gene Med. 2005; 7(3):316-24), catheter-based antegrade intracoronary delivery with coronary venous blockade (Hayase et al., Am. J. Physiol. Heart Circ. Physiol. 2005; 288(6):H2995-3000), aortic and pulmonary artery cross clamping followed by proximal aortic injection of adeno-associated viral vector (Kaspar et al., J. Gene Med. 2005; 7(3):316-24). Leiden and Svensson mention in vivo infusion of a rAAV vector into a coronary artery or sinus generally, but only describe in detail the perfusion of a mouse heart with a reporter gene ex vivo at 4° C. where the heart has stopped beating (WO 00/38518)—a method that is impractical for the treatment of large mammals, such as humans.

Thus, these methods are all inadequate for use in a clinical setting, for example because these methods are too risky due to the need for surgical intervention or interruption of flow of oxygenated blood to the heart muscle, because of the amount of viral vector required to practice the method, because of the low percentage of tissue transfected, because the fact that transduction is limited to the site of the injection/administration only, or because the method is not practical or unproven for the treatment of disease in large animals or humans. There remains a need for a simple, minimally invasive, yet effective means of delivering transgenes using viral vectors to cardiac tissue to treat a disease, particularly in humans.

For instance, previously described in U.S. patent application Ser. No. 11/778,900 (incorporated herein by reference in its entirety) is a method of transfection of cardiac cells using a slow infusion of a therapeutic polynucleotide into coronary vessels. Increasing the efficiency of transfection of cardiac cells with the polynucleotide can lead to an increase in the efficacy of the treatment.

Use of nitroglycerin as part of a pretreatment cocktail has been used in myocardial gene transfer therapy in animals (see Sasano T., et al., "Targeted High-Efficiency, Homogenous Myocardial Gene Transfer" in J. Mol. Cell. Cardiol., May 2007; 42(5):954-961, which is hereby incorporated by reference in its entirety, describes pig experiments involving myocardial gene transfer using a viral vector). In an effort to increase the efficiency of gene transfer in normal healthy pigs, they report using a pretreatment cocktail comprising vascular endothelial growth factor (VEGF), nitroglycerin, adenosine and calcium, followed by dosing with the viral vector and combinations of the above mentioned agents. However, their treatment protocols are not clinically practical as such protocols would lead to prohibitive hypotension and cardiac side-effects. For example, Sasano reports that "infusion of the pretreatment and virus solutions caused an immediate systolic blood pressure decrease of 30 mmHg that stabilized within the first minute of perfusion. The average heart rate also decreased to 50-60/min then stabilized over the same time course." The authors reported further, "ventricular fibrillation (VF) occurred during coronary infusion in 5 of the first 10 pigs (50%) and 4 out of remaining 71 pigs (5.6%)" (Sasano et al. at pg. 958). Given the frail status of most human subjects with advanced cardiac disease, these side effects are likely even less tolerable than in young, normal, healthy animals.

Thus, there still exists a need to develop a treatment method for increasing the efficiency of cardiac transfection using vasodilation and viral vectors such as adeno-associated virus (AAV) that can be used in a clinical setting, without incurring life-threatening hypotension or cardiac arrhythmias.

SUMMARY OF THE INVENTION

The present invention relates to uses and therapies for the treatment of heart diseases, particularly to improving or enhancing the delivery of therapeutic agents to heart tissue by the use of a vasodilator agent, preferably a nitric oxide (NO) increasing substance, by direct intracoronary, intravenous, or subcutaneous injection or infusion, or oral administration, without the need for obstructing blood flow.

A preferred embodiment of the invention is a method of treating or preventing a cardiovascular disease by transfecting cardiac cells of a large mammal, the method comprising identifying a mammal in need of treatment or prevention of a cardiovascular disease; administering a vasodilating substance to said mammal sufficient to dilate a blood vessel of the coronary circulation; and administering a therapeutic polynucleotide into a blood vessel of the coronary circulation in vivo; wherein said therapeutic polynucleotide is infused into said blood vessel over a period of at least about three minutes, wherein the coronary circulation is not isolated or substantially isolated from the systemic circulation of the mammal, and wherein said therapeutic polynucleotide transfects cardiac cells of said mammal resulting in the treatment or prevention of said cardiovascular disease. In some embodiments, said vasodilating substance is a NO increasing substance. In some embodiments, said NO increasing substance is nitroglycerin.

In some embodiments, said NO increasing substance is administered into a blood vessel of the coronary circulation. In some embodiments, said NO increasing substance is administered in a manner selected from the group consisting of: prior to said infusion of said therapeutic polynucleotide, concurrently with said infusion of said therapeutic polynucleotide, and prior to and concurrently with said infusion of said therapeutic polynucleotide. In some embodiments, said NO increasing substance is administered as a bolus injection not more than 5 minutes prior to said infusion of said therapeutic polynucleotide.

In some embodiments, said NO increasing substance is administered as a bolus injection not more than 5 minutes prior to said infusion of said therapeutic polynucleotide and said NO increasing substance is infused into said blood vessel concurrently with said infusion of said therapeutic polynucleotide over a period of at least about 10 minutes.

In some embodiments, the NO increasing substance is about 50 µg to about 150 µg of nitroglycerin.

In some embodiments, administration of said NO increasing substance comprises antegrade epicardial coronary artery injection of 1.5 mL of a 100 µg/mL solution of nitroglycerin into at least one of a left or right coronary artery via percutaneous catheter over a period of less than 1 minute, wherein said administration of said NO increasing substance is less than 3 minutes prior to said infusion of said therapeutic polynucleotide, and wherein no other vasodilator or vascular permeation enhancer is administered to said mammal. In some embodiments, the method further comprises infusing nitroglycerin into said blood vessel concurrently with said infusion of said therapeutic polynucleotide. In some embodiments, said mammal is a human and said cardiovascular disease is heart failure, wherein said therapeutic polynucleotide is packaged in a DNAse resistant particle (DRP) of a AAV2/1 viral vector, and a total number of DRP infused into said blood vessel is not more than about $1 \times 10^{13}$, wherein the therapeutic polynucleotide comprises a SERCA2a coding sequence, wherein said blood vessel is at least one of the left or right coronary artery, and wherein said infusion of said therapeutic polynucleotide lasts at least about 10 minutes. In some embodiments, said treatment improves a measurement of absolute ejection fraction of said human's heart six months after said treatment as compared to a measurement of absolute ejection fraction of said human's heart prior to said treatment.

In some embodiments, said NO increasing substance is administered systemically. In some embodiments, said NO increasing substance is administered systemically in a manner selected from the group consisting of: intravenous injection, intravenous infusion, oral administration, transdermal administration, and subcutaneous administration.

In some embodiments, said NO increasing substance is administered in a manner selected from the group consisting of: prior to said infusion of said therapeutic polynucleotide, concurrently with said infusion of said therapeutic polynucleotide, and prior to and concurrently with said infusion of said therapeutic polynucleotide.

In some embodiments, about 0.5 mg to about 2.5 mg of nitroglycerin is administered by intravenous infusion over a period of at least 30 minutes prior to said infusion of said therapeutic polynucleotide, wherein said infusion of said therapeutic polynucleotide begins within not more than three minutes of the completion of said intravenous infusion of nitroglycerin, and wherein no other vasodilator or vascular permeation enhancer is administered to said mammal. In some embodiments, the method further comprises infusing an additional amount of nitroglycerin concurrently with said infusion of said therapeutic polynucleotide. In some embodiments, said mammal is a human and said cardiovascular disease is heart failure, wherein said therapeutic polynucleotide is packaged in a DNAse resistant particle (DRP) of a AAV2/1 viral vector, and a total number of DRP infused into said blood vessel is not more than about $1 \times 10^{13}$, wherein the therapeutic polynucleotide comprises a SERCA2a coding sequence, wherein said blood vessel is at least one of the left or right coronary artery, and wherein said infusion of said therapeutic polynucleotide lasts at least about 10 minutes. In some embodiments, said treatment improves a measurement of absolute ejection fraction of said human's heart six months after said treatment as compared to a measurement of absolute ejection fraction of said human's heart prior to said treatment.

An embodiment of the invention is a therapeutic polynucleotide for use in a method of treating or preventing a cardiovascular disease by transfecting cardiac cells of a large mammal, wherein the method comprises dilating a blood vessel of the coronary circulation by administering a vasodilating substance to said mammal prior to, and/or concurrent with, administering said therapeutic polynucleotide. In some embodiments, the method comprises administering the therapeutic polynucleotide into a blood vessel of the coronary circulation in vivo, wherein said therapeutic polynucleotide is infused into said blood vessel over a period of at least about three minutes, wherein the coronary circulation is not isolated or substantially isolated from the systemic circulation of the mammal, and wherein said therapeutic polynucleotide transfects cardiac cells of said mammal resulting in the treatment or prevention of said cardiovascular disease.

In some embodiments, said vasodilating substance is a NO increasing substance. In some embodiments, said NO increasing substance is administered in a manner selected from the group consisting of: prior to said infusion of said therapeutic polynucleotide, concurrently with said infusion of said therapeutic polynucleotide, and prior to and concurrently with said infusion of said therapeutic polynucleotide.

In some embodiments, said NO increasing substance is administered into a blood vessel of the coronary circulation. In some embodiments, said NO increasing substance is administered as a bolus injection not more than 5 minutes prior to said infusion of said therapeutic polynucleotide and wherein said NO increasing substance is infused into said blood vessel concurrently with said infusion of said therapeutic polynucleotide over a period of at least about 10 minutes.

In some embodiments, the NO increasing substance is about 50 µg to about 150 µg of nitroglycerin.

In some embodiments, said administration of said NO increasing substance comprises antegrade epicardial coronary artery injection of 1.5 mL of a 100 µg/mL solution of nitroglycerin into at least one of a left or right coronary artery via percutaneous catheter over a period of less than 1 minute, wherein said administration of said NO increasing substance is less than 3 minutes prior to said infusion of said therapeutic polynucleotide, and wherein no other vasodilator or vascular permeation enhancer is administered to said mammal. In some embodiments, the method further comprises infusing nitroglycerin into said blood vessel concurrently with said infusion of said therapeutic polynucleotide. In some embodiments, said mammal is a human and said cardiovascular disease is heart failure, wherein said therapeutic polynucleotide is packaged in a DNAse resistant particle (DRP) of a AAV2/1 viral vector, and a total number of DRP infused into said blood vessel is not more than about $1\times10^{13}$, wherein the therapeutic polynucleotide comprises a SERCA2a coding sequence, wherein said blood vessel is at least one of the left or right coronary artery, and wherein said infusion of said therapeutic polynucleotide lasts at least about 10 minutes. In some embodiments, said method of treating or preventing improves a measurement of absolute ejection fraction of said human's heart six months after said treatment as compared to a measurement of absolute ejection fraction of said human's heart prior to said treatment.

In some embodiments, said NO increasing substance is administered systemically in a manner selected from the group consisting of: intravenous injection, intravenous infusion, oral administration, transdermal administration, and subcutaneous administration. In some embodiments, said administration of said NO increasing substance comprises administering about 0.5 mg to about 2.5 mg of nitroglycerin by intravenous infusion over a period of at least 30 minutes prior to said infusion of said therapeutic polynucleotide, wherein said infusion of said therapeutic polynucleotide begins within not more than three minutes of the completion of said intravenous infusion of nitroglycerin, and wherein no other vasodilator or vascular permeation enhancer is administered to said mammal. In some embodiments, said method further comprises infusing an additional amount of nitroglycerin concurrently with said infusion of said therapeutic polynucleotide. In some embodiments, said mammal is a human and said cardiovascular disease is heart failure, wherein said therapeutic polynucleotide is packaged in a DNAse resistant particle (DRP) of a AAV2/1 viral vector, and a total number of DRP infused into said blood vessel is not more than about $1\times10^{13}$, wherein the therapeutic polynucleotide comprises a SERCA2a coding sequence, wherein said blood vessel is at least one of the left or right coronary artery, and wherein said infusion of said therapeutic polynucleotide lasts at least about 10 minutes. In some embodiments, said method of treating or preventing improves a measurement of absolute ejection fraction of said human's heart six months after said treatment as compared to a measurement of absolute ejection fraction of said human's heart prior to said treatment.

Another embodiment of the invention is the use of a therapeutic polynucleotide for the manufacture of a medicament for treating or preventing a cardiovascular disease in a large mammal, wherein the therapeutic polynucleotide transfects cardiac cells of said large mammal resulting in the treatment or prevention of said cardiovascular disease, and wherein said medicament is for administration in combination with a vasodilating substance that dilates a blood vessel of the coronary circulation of said mammal prior to, and/or concurrent with, administration of said medicament. In some embodiments, the administration of the medicament comprises administering the therapeutic polynucleotide into a blood vessel of the coronary circulation in vivo, wherein said therapeutic polynucleotide is infused into said blood vessel over a period of at least about three minutes, and wherein the coronary circulation is not isolated or substantially isolated from the systemic circulation of the mammal. In some embodiments, said vasodilating substance is a nitric oxide (NO) increasing substance. In some embodiments, said NO increasing substance is administered in a manner selected from the group consisting of: prior to said infusion of said therapeutic polynucleotide, concurrently with said infusion of said therapeutic polynucleotide, and prior to and concurrently with said infusion of said therapeutic polynucleotide.

In some embodiments, said NO increasing substance is administered into a blood vessel of the coronary circulation. In some embodiments, said NO increasing substance is administered as a bolus injection not more than 5 minutes prior to said infusion of said therapeutic polynucleotide and wherein said NO increasing substance is infused into said blood vessel concurrently with said infusion of said therapeutic polynucleotide over a period of at least about 10 minutes. In some embodiments, the NO increasing substance is about 50 µg to about 150 µg of nitroglycerin.

In some embodiments, said administration of said NO increasing substance comprises antegrade epicardial coronary artery injection of 1.5 mL of a 100 µg/mL solution of nitroglycerin into at least one of a left or right coronary artery via percutaneous catheter over a period of less than 1 minute, wherein said administration of said NO increasing substance is less than 3 minutes prior to said infusion of said therapeutic polynucleotide, and wherein no other vasodilator or vascular permeation enhancer is administered to said mammal. In some embodiments, the method further comprises infusing nitroglycerin into said blood vessel concurrently with said infusion of said therapeutic polynucleotide. In some embodiments, said mammal is a human and said cardiovascular disease is heart failure, wherein said therapeutic polynucleotide is packaged in a DNAse resistant particle (DRP) of a AAV2/1 viral vector, and a total number of DRP infused into said blood vessel is not more than about $1\times10^{13}$, wherein the therapeutic polynucleotide comprises a SERCA2a coding sequence, wherein said blood vessel is at least one of the left or right coronary artery, and wherein said infusion of said therapeutic polynucleotide lasts at least about 10 minutes. In some embodiments, said method of treating or preventing improves a measurement of absolute ejection fraction of said human's heart six months after said treatment as compared to a measurement of absolute ejection fraction of said human's heart prior to said treatment.

In some embodiments, said NO increasing substance is administered systemically in a manner selected from the group consisting of: intravenous injection, intravenous infusion, oral administration, transdermal administration, and subcutaneous administration. In some embodiments, administration of said NO increasing substance comprises administering about 0.5 mg to about 2.5 mg of nitroglycerin by intravenous infusion over a period of at least 30 minutes prior to said infusion of said therapeutic polynucleotide, wherein said infusion of said therapeutic polynucleotide begins within not more than three minutes of the completion of said intravenous infusion of nitroglycerin, and wherein no other vasodilator or vascular permeation enhancer is administered to said mammal. Some embodiments further comprise infusing an additional amount of nitroglycerin concurrently with said infusion of said therapeutic polynucleotide. In some embodiments, said mammal is a human and said cardiovascular disease is heart failure, wherein said therapeutic polynucleotide is packaged in a DNAse resistant particle (DRP) of a AAV2/1 viral vector, and a total number of DRP infused into said blood vessel is not more than about $1\times10^{13}$, wherein the therapeutic polynucleotide comprises a SERCA2a coding sequence, wherein said blood vessel is at least one of the left or right coronary artery, and wherein said infusion of said therapeutic polynucleotide lasts at least about 10 minutes. In some embodiments, said method of treating or preventing improves a measurement of absolute ejection fraction of said human's heart six months after said treatment as compared to a measurement of absolute ejection fraction of said human's heart prior to said treatment.

In some of the embodiments, said NO increasing substance comprises nitroglycerin. In some embodiments, said NO increasing substance consists essentially of nitroglycerin. In some embodiments, said NO increasing substance consists of nitroglycerin. In some embodiments, no other vasodilator or vascular permeation enhancer is administered to said mammal.

In some embodiments, the outflow of the coronary circulation is not nonnaturally restricted.

In some embodiments, transfection of cardiac cells of the anterior lateral ventricle, inferior lateral ventricle, septum and right ventricle is detectable using quantitative PCR (RNA or DNA).

In some embodiments, the polynucleotide is capable of expressing a protein capable of modulating a cellular activity of the cardiac cells. In some embodiments, said cellular activity is a calcium cycling pathway of a cardiomyocyte. In some embodiments, said protein is a sarcoplasmic/endoplasmic reticulum ATPase (SERCA). In some embodiments, the SERCA is SERCA2a.

In some embodiments, said polynucleotide is present in a viral vector selected from the group consisting of an adeno-associated virus, an adenovirus, a retrovirus, a herpes simplex virus, a bovine papilloma virus, a lentiviral vector, a vaccinia virus, and a polyoma virus. In some embodiments, said viral vector is AAV virus. In some embodiments, said viral vector is AAV virus comprising heterologous capsid proteins such that capsid proteins VP1, VP2 and VP3 are not all of the same serotype AAV. In some embodiments, said heterologous capsid proteins comprise capsid proteins from AAV1 and AAV2. In some embodiments, said viral vector is an AAV2/1 vector. In some embodiments, said polynucleotide is operably linked to a CMV-based promoter and packaged in said viral vector. In some embodiments, said polynucleotide comprises a SERCA2a coding sequence.

In some embodiments, said transfection of said cardiac cells increases lateral ventricle fractional shortening. In some embodiments, said mammal is human and said disease is congestive heart failure. In some embodiments, said transfection of said cardiac cells increases lateral ventricle fractional shortening when measured about 4 months after said infusion by at least 25% as compared to lateral ventricle fractional shortening before infusion of the polynucleotide. In some embodiments, said transfection of said cardiac cells results in an improvement in a measure of cardiac function selected from the group consisting of expression of SERCA2a protein, fractional shortening, ejection fraction, cardiac output, time constant of ventricular relaxation, and regurgitant volume.

In some embodiments the infusion into the blood vessel is at a rate of less than or equal to about 6.0 mL/min, in some it is at a rate of less than or equal to about 2.5 mL/min, in some it is at a rate of less than or equal to about 2.0 mL/min, in some it is at a rate of less than or equal to about 1.2 mL/min, in some it is at a rate of less than or equal to about 1.0 mL/min, in some is at a rate of less than or equal to about 0.6 mL/min.

In a preferred embodiment, the polynucleotide is present in a viral vector selected from the group consisting of an adeno-associated virus, an adenovirus, a retrovirus, a herpes simplex virus, a bovine papilloma virus, a lentiviral vector, a vaccinia virus, and a polyoma virus. In a more preferred embodiment, the viral vector is AAV virus or an AAV molecular variant (see Li et al., Molecular Therapy vol. 16 no. 7 Jul. 2008, pg. 1252-1260, incorporated herein by reference in its entirety), and in a more preferred embodiment the viral vector is an AAV2/1 vector. The AAV2/1 vector consists of an AAV serotype 1 capsid and Inverted Terminal Repeats (ITRs) derived from AAV serotype 2. In some embodiments, the polynucleotide is operably linked to a CMV-based promoter and packaged in the viral vector. In a preferred embodiment, the polynucleotide comprises a human SERCA2a cDNA. Preferably, the vector consists of an AAV serotype 1 capsid and contains the human SERCA2a cDNA flanked by Inverted Terminal Repeats (ITRs) derived from AAV serotype 2 (AAV1/SERCA2a).

A preferred embodiment of the invention is a method of treating or preventing a heart disease by transfecting cardiac cells of a large mammal, the method comprising: injecting between 50 and 150 micrograms of nitroglycerin via intracoronary bolus injection lasting less than one minute into a coronary blood vessel; infusing between about $1.4 \times 10^{11}$ to about $1 \times 10^{13}$ DRP of AAV1/SERCA2a into a blood vessel of the coronary circulation in vivo, where the AAV1/SERCA2a is infused into the blood vessel over a period of at least about three minutes, where the coronary circulation is not isolated or substantially isolated from the systemic circulation of the mammal; and where the AAV1/SERCA2a transfects cardiac cells of the mammal resulting in the treatment or prevention of the heart disease. In a preferred embodiment, nitroglycerin is the only vasodilator or permeability enhancer administered, and no other vasodilator or permeability enhancer is administered.

DETAILED DESCRIPTION OF THE PREFERRED EMBODIMENT

Figure 1:
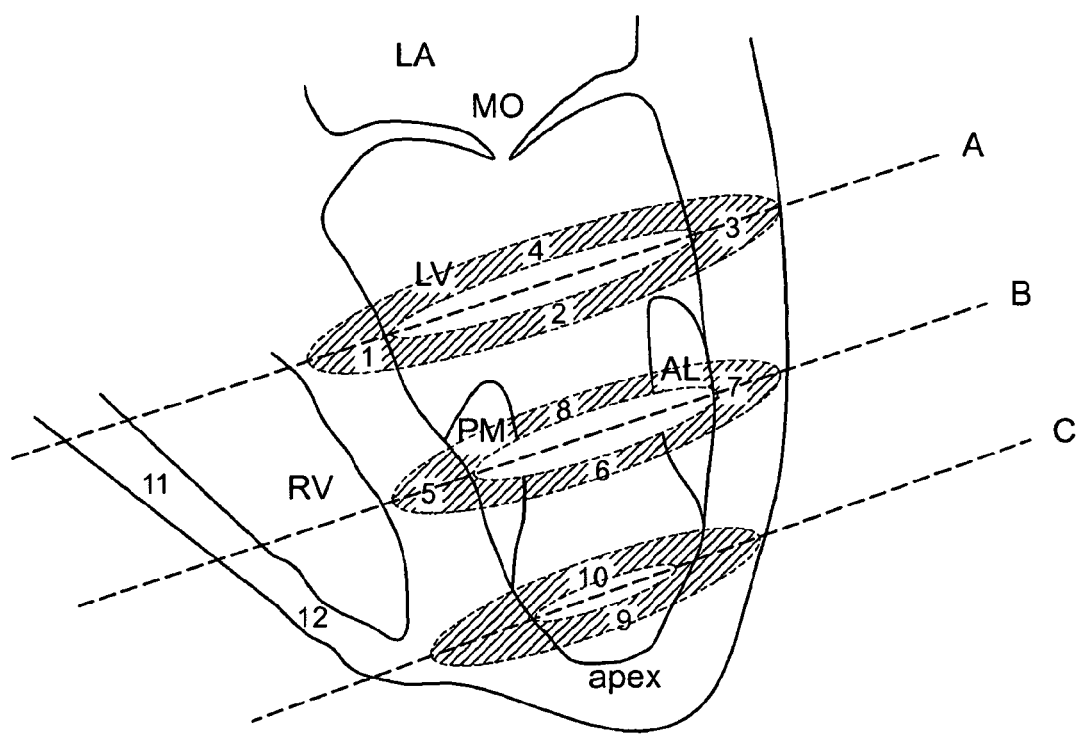
FIG. 1. Map of heart sections tested for expression of SERCA2a in normal Göttingen Minipigs. (A) basal layer of left ventricle (LV), (B) middle layer of LV, (C) apical layer of LV.

The present technology relates to uses and therapies for the treatment of heart diseases, particularly to enhancing the delivery of therapeutic agents to heart tissue with vasodilators without the need for obstructing blood flow. A preferred embodiment of the invention is a method of treating or preventing a heart disease by transfecting cardiac cells of a large mammal, the method comprising: identifying a mammal in need of treatment or prevention of a cardiac disease; injecting or infusing a substance to increase vasodilation preferably by increasing the amount of nitric oxide in the coronary circulation; infusing a therapeutic polynucleotide into a blood vessel of the coronary circulation in vivo, where the therapeutic polynucleotide is infused into the blood vessel over a period of at least about three minutes, where the coronary circulation is not isolated or substantially isolated from the systemic circulation of the mammal; and where the therapeutic polynucleotide transfects cardiac cells of the mammal resulting in the treatment or prevention of the heart disease.

As used herein, "polynucleotide" has its ordinary and customary meaning in the art and includes any polymeric nucleic acid such as DNA or RNA molecules, as well as chemical derivatives known to those skilled in the art. Polynucleotides include not only those encoding a therapeutic protein, but also include sequences that can be used to decrease the expression of a targeted nucleic acid sequence using techniques known in the art (e.g., antisense, interfering, or small interfering nucleic acids). One example is a sequence which reduces or eliminates the expression of phospholamban. Polynucleotides can also be used to initiate or increase the expression of a targeted nucleic acid sequence or the production of a targeted protein within cells of the cardiovascular system. Targeted nucleic acids and proteins include, but are not limited to, nucleic acids and proteins normally found in the targeted tissue including naturally occurring mutations, derivatives of such naturally occurring nucleic acids or proteins, naturally occurring nucleic acids or proteins not normally found in the targeted tissue, or synthetic nucleic acids or proteins. One or more polynucleotides can be used in combination, administered simultaneously and/or sequentially, to increase and/or decrease one or more targeted nucleic acid sequences or proteins.

As used herein the terms "infusion," "infused," and "infusing" have their ordinary and customary meaning in the art and refer to administration for a time period (typically a minute or more) that is substantially longer than the art recognized term of "injection" or "bolus injection," (typically less than a minute). The flow rate of the infusion will depend at least in part on the volume administered, however the flow rate of an "infusion" is slower than that of an "injection" for the same volume.

An "effective amount" has its ordinary and customary meaning in the art and includes an amount sufficient to effect or achieve a beneficial or desired therapeutic effect. For example, an "effective amount" is an amount that achieves any of the following: an increase in lateral ventricle fractional shortening; and/or palliation, amelioration, stabilization, reversal, slowing or delay in the progression or a sign or symptom of the disease state. An effective amount can be administered in one or more administrations.

As used herein "in conjunction with," "in combination with," "concurrent," or "concurrently," have their ordinary and customary meaning in the art and include administration of one treatment modality in addition to another treatment modality. For example, infusion of a polynucleotide to a subject can be carried out in addition to administer a pharmaceutical composition or compositions to the same individual. As used herein, these terms include simultaneous administration, or nearly simultaneous administration.

The disclosed methods and therapeutic agents disclosed herein can be combined with existing treatments for cardiac disease, including those listed above in the introduction, such as drugs and percutaneous or surgical intervention, to provide an enhanced therapeutic effect compared to existing treatments alone. An enhanced therapeutic effect may be demonstrated by, for example, an extension of the time period between the worsening of the signs or symptoms of the disease compared to the average or typical time period for existing treatment regimens, or the lengthening of time required before additional treatment is required compared to the average or typical time for standard treatment alone.

As used herein, "treat" or "treatment" of disease has its ordinary and customary meaning in the art and includes the stabilization, cure, or less than complete cure of a disease, including the halting or slowing of the progression of a disease or a sign or symptom of the disease. The term "prevention" has its ordinary and customary meaning in the art and includes complete or incomplete prevention, or a delay of the onset of, a disease or a sign or symptom of a disease. The terms "therapeutic," "therapeutic effect" or "clinical effect" includes both treatment and prevention. Examples of diseases intended to be treated using the present technology that are associated with the cardiovascular system include, but are not limited to, heart failure, ischemia, arrhythmia, myocardial infarction, congestive heart failure, transplant rejection, abnormal heart contractility, non-ischemic cardiomyopathy, mitral valve regurgitation, aortic stenosis or regurgitation, abnormal $Ca^{2+}$ metabolism and congenital heart disease. For example, beneficial or desired clinical results or therapeutic effects include, but are not limited to, increased survival, a greater alleviation of signs or symptoms of cardiovascular disease, increased diminishment of extent of disease, stabilization (i.e., not worsening) of disease state, delay or slowing of disease progression, amelioration or palliation of the disease state, and remission (whether partial or total), whether detectable or undetectable. Other examples of therapeutic effect include, but are not limited to, increased lateral ventricle fractional shortening; augmented cardiac contractility at the cellular and intact animal levels, reversal of cardiac remodeling, and normalization of the abnormally high diastolic levels of cytosolic calcium. Other clinical features which can be improved in a subject treated with an embodiment of the present invention include without limitation survival, cardiac metabolism, heart contractility, heart rate, ventricular function (e.g., left ventricular ejection fraction (LVEF), left ventricular end-systolic volume (LVESV), end-diastolic pressure (LVEDP), left ventricular systolic pressure (LVSP)), $Ca^{2+}$ metabolism (e.g., intracellular $Ca^{2+}$ concentration, peak or resting $[Ca^{2+}]$, SR $Ca^{2+}$ ATPase activity, phosphorylation state of phospholamban), force generation, relaxation and pressure of the heart, a force frequency relationship, cardiocyte survival or apoptosis or ion channel activity (e.g., sodium calcium exchange, sodium channel activity, calcium channel activity, sodium potassium ATPase pump activity), activity of myosin heavy chain, troponin I, troponin C, troponin T, tropomyosin, actin, myosin light chain kinase, myosin light chain 1, myosin light chain 2 or myosin light chain 3, IGF-1 receptor, PI3 kinase, AKT kinase, sodium-calcium exchanger, calcium channel (L and T), calsequestrin, calreticulin, inhibitor-1 of the type 1 protein phosphatase, or any agent promoting dephosphorylation of phospholamban or inhibitor of the sarcoplasmic reticulum calcium-pump (SERCA2a). Other measures of cardiac disease which can be improved include fractional shortening, cardiac output, ejection fraction, Tau, regurgitant volume, reduced hospital stays, improved quality of life, increased treadmill time, increased distance during 6 minute walk test, and increased maximal oxygenated consumption ($VO_2$max).

As used herein, "exogenous" nucleic acids or genes are those that do not occur in nature in the vector utilized for nucleic acid transfer; e.g., not naturally found in the viral vector, but the term is not intended to exclude nucleic acids encoding a protein or polypeptide that occurs naturally in the patient or host, e.g., SERCA.

As used herein, "cardiac cell" includes any cell of the heart that is involved in maintaining a structure or providing a function of the heart such as a cardiac muscle cell, a cell of the cardiac vasculature, or a cell present in a cardiac valve. Cardiac cells include cardiomyocytes (having both normal and abnormal electrical properties), epithelial cells, endothelial cells, fibroblasts, cells of the conducting tissue, cardiac pace-making cells, and neurons.

As used herein, "isolated," "substantially isolated" or "largely isolated" and their variants are terms that do not require complete or absolute isolation of the coronary venous, cardiac, systemic venous, or systemic circulation; rather, they are intended to mean that a majority, preferably the major part or even substantially all of the specified circulation is isolated. As used herein, "partially isolated" refers to any nontrivial portion of the specified circulation being isolated.

As used herein, "nonnaturally restricted" includes any method of restricting the flow of fluid through a blood vessel, e.g., balloon catheter, sutures, etc., but does not include naturally occurring restriction, e.g. plaque build-up (stenosis). Nonnatural restriction includes substantial or total isolation of, for example, the coronary circulation.

As used herein, "modulating" has its ordinary meaning, and encompasses both increasing and decreasing the expression or activity of the target.

As used herein, the term "minimally invasive" is intended to include any procedure that does not require open surgical access to the heart or vessels closely associated with the heart. Such procedures include the use of endoscopic means to access the heart, and also catheter-based means relying on access via large arteries and veins, such as the femoral artery.

As used herein, the term "adeno-associated virus" or "AAV" encompasses all subtypes, serotypes and pseudotypes, as well as naturally occurring and recombinant forms or molecular variants (see Li et al). A variety of AAV serotypes and strains are known in the art and are publicly available from sources, such as the ATCC, and academic or commercial sources. Alternatively, sequences from AAV serotypes and strains which are published and/or available from a variety of databases may be synthesized using known techniques.

As used herein, the term "serotype" refers to an AAV which is identified by and distinguished from other AAVs based on capsid protein reactivity with defined antisera. There are at least twelve known serotypes of human AAV, including AAV1 through AAV12, however additional serotypes continue to be discovered, and use of newly discovered serotypes are contemplated. For example, AAV2 serotype is used to refer to an AAV which contains capsid proteins encoded from the cap gene of AAV2 and a genome containing 5' and 3' inverted terminal repeat (ITR) sequences from the same AAV2 serotype.

A "pseudotyped" AAV refers to an AAV that contains capsid proteins from one serotype and a viral genome including 5' and 3' inverted terminal repeats (ITRs) of a different or heterologous serotype. A pseudotyped rAAV would be expected to have cell surface binding properties of the capsid serotype and genetic properties consistent with the ITR serotype. A pseudotype rAAV may comprise AAV capsid proteins, including VP1, VP2, and VP3 capsid proteins, and ITRs from any serotype AAV, including any primate AAV serotype from AAV1 through AAV12, as long as the capsid protein is of a serotype heterologous to the serotype(s) of the ITRs. In a pseudotype rAAV, the 5' and 3' ITRs may be identical or heterologous. Pseudotyped rAAV are produced using standard techniques described in the art.

A "chimeric" rAAV vector encompasses an AAV vector comprising heterologous capsid proteins; that is, a rAAV vector may be chimeric with respect to its capsid proteins VP1, VP2 and VP3, such that VP1, VP2 and VP3 are not all of the same serotype AAV. A chimeric AAV as used herein encompasses AAV wherein the capsid proteins VP1, VP2 and VP3 differ in serotypes, including for example, but not limited to, capsid proteins from AAV1 and AAV2, mixtures of other parvovirus capsid proteins or comprise other virus proteins or other proteins, such as for example, proteins that target delivery of the AAV to desired cells or tissues. A chimeric rAAV as used herein also encompasses a rAAV comprising chimeric 5' and 3' ITRs. The present invention encompasses chimeric rAAV vectors that comprise ITRs from different AAV serotypes, for example AAV1 and AAV2, or a chimeric rAAV may comprise synthetic sequences.

Vasodilators

Vasodilation is the widening of blood vessels that occurs from relaxation of smooth muscle within the vessel walls, arteries, arterioles, veins, and venules. As a result of vasodilation, vascular resistance decreases and the flow of blood increases. Intrinsic and extrinsic factors can induce vasodilation; such factors are called vasodilators. There are two general mechanisms that cause vasodilation: lowering of intracellular calcium and/or dephoshorylation of the myosin light chain (MLC). These mechanisms are carried out through three general pathways: hyperpolarization-mediated, cAMP-mediated, or cGMP-mediated. Thus, vasodilators may exert their effects through one or more of these intermediary pathways. In one embodiment, a vasodilator may include, but is not limited to, adenosine, histamine (or histamine-inducing agents), alpha blockers, theobromine, papaverine, ethanol, tetrahydrocannabinol(THC), minoxidil, or nitric oxide (including nitric oxide increasing substances). In one embodiment, only a single vasodilating substance is administered. In another embodiment, it is contemplated to use one or more vasodilators together, sequentially, or a combination thereof. In a preferred embodiment, the vasodilator is a nitric oxide increasing substance.

Nitric oxide (NO) is a free radical molecule, which can act as a short lived chemical transmitter, freely diffusible across membranes. NO has a variety of physiological effects. See generally, Jeremy M. Berg, et al. (2006), Biochemistry, 6th Edition. W. H. Freeman and Company. For example, it is known to cause vascular dilatation by controlling smooth muscle contractility after systemic or local delivery. In the central nervous system, NO can affects synaptic transmission stimulating learning and memory capacity. As another example, NO can induce platelet aggregation in blood plasma. Because of its lipophilic nature, nitric oxide can diffuse out of its cells of origin into other nearby cells, creating a signal transduction mechanism. In the coronary arteries, NO can activate cytosolic guanylate cyclase and stimulate cyclic guanosine monophosphate (cGMP) formation in vascular smooth muscle cells, leading to vasodilation.

Without limitation to any specific mechanism of action, it has been discovered that vasodilation of the coronary circulation, or in an artery supplying blood to the heart, can increase the efficiency of transduction of the therapeutic agent described further below. That is, transduction efficiency of the therapeutic agent can be enhanced by administering to the coronary circulation, cardiac artery, or systemically, a vasodilating agent or combination of agents capable of inducing vasodilation, preferably, with a NO increasing substance. As used herein, "NO increasing substance" includes combinations of two, three, four, five or more compounds unless indicated otherwise, and can include compounds that mimic an increase in NO by activating the receptor for NO, e.g. a NO agonist, without actually increasing the amount of NO. In some embodiments, the treatment can occur before, at least partially during, or after treatment with the primary agent. Thus, in some embodiments, NO can be used as an adjuvant to increase the efficiency, efficacy, or potency of the primary therapeutic agent. Embodiments include combinations of two, three, four, five, or more NO increasing substances.

Increasing levels of NO, even temporarily, in the coronary circulation can be accomplished by a variety of known techniques. As used herein, NO increasing substance includes, but is not limited to, any of the following compounds or classes of compounds, or any combination of two, three, four, five or more of the following compounds or classes of compounds. Agents that release NO under physiological conditions have been in use for a long time in the management of heart diseases. These agents can include, by way of example only, NO donors, NO releasing molecules, NO precursors. For example, NO donors can include nitrates such as glyceryl trinitrate, which may also be commonly referred to as "nitroglycerin." Other examples of nitrates include isosorbide dinitrate and isosorbide mononitrate. NO donors can also include other agents such as those described in Megson I L, Webb D J, "Nitric oxide donor drugs: current status and future trends" in Expert. Opin. Investig. Drugs, May 2002;11(5):587-601, which is hereby incorporated by reference in its entirety. NO releasing molecules can also increase the levels of NO in the coronary circulation or a coronary artery. For example, NO releasing molecules can include diazeniumdiolates or NO releasing non-steroidal anti-inflammatory drugs (NO-NSAID). NO precursors, such as L-arginine, can also be used to increase levels of NO. Other nitric oxidide increasing substances that can be used include molecular nitric oxide, nicorandil, and nitric oxide synthase, sodium nitroprusside, and pentaerythritol tetranitrate (PETN). Moreover, agents that increase the effects of NO are also contemplated such as phosphodiesterase type 5 (PDE5) inhibitors including, but not limited to, sildenafil, tadalafil, and vardenafil.

In some embodiments, the substance used to increase the amount of nitric oxide in the coronary circulation comprises a nitric oxide donor. In some embodiments, the nitric oxide donor comprises a nitrate. In a preferred embodiment, the nitrate comprises glyceryl trinitrate. In some embodiments, the nitrate comprises an agent selected from the group consisting of pentaerythritol tetranitrate, isosorbide dinitrate and isosorbide-mononitrate. In some embodiments, the nitric oxide donor comprises sodium nitroprusside. In some embodiments, the substance used to increase the amount of nitric oxide in the coronary circulation comprises a nitric oxide releasing molecule. In some embodiments, the nitric oxide releasing molecule comprises an agent selected from the group consisting of a diazeniumdiolates and a nitric oxide-releasing non-steroidal anti-inflammatory drugs. In some embodiments, the substance used to increase the amount of nitric oxide in the coronary circulation comprises an agent selected from the group consisting of molecular nitric oxide, nicorandil, and nitric oxide synthase. In some embodiments, the substance used to increase the amount of nitric oxide in the coronary circulation comprises a nitric oxide precursor. In some embodiments, the nitric oxide precursor comprises L-arginine.

Vasodilating Substance Administration

The vasodilating substance or substances can be administered systemically, for example orally, including but not limited to sublingual and translingual administration, transdermally, including but not limited to via a patch or ointment, or by intravenous injection or infusion. In a preferred embodiment, the vasodilating substance or substances can be administered by intracoronary injection or infusion. In another preferred embodiment, the vasodilating substance or substances can be administered by intravenous infusion or injection. The following sections describe further these modes of delivery.

The coronary circulation provides blood supply to the tissue of the heart. Intracoronary administration is accomplished by injection or infusion into one or more blood vessel of the coronary circulation of the beating heart in vivo. There are a number of coronary arteries. Normally, four main coronary arteries provide oxygenated blood to the heart for distribution throughout the heart tissue: the left main and right coronary arteries, the left anterior descending artery, and the left circumflex artery. Injection or infusion of one or a combination of these arteries is contemplated, for example injection or infusion into the left and right coronary arteries. In one embodiment, ⅔ of the total amount of a vasodilating substance or substances, including but not limited to a NO increasing substance or substances, is delivered to one blood vessel of the heart, and ⅓ is administered to another blood vessel of the heart. In another embodiment, more than 2 coronary blood vessels are injected or infused, (e.g. 3, 4, 5 or more), and the portion of total volume or amount of vasodilator administered per blood vessel can be adjusted as appropriate. The preferred embodiment utilizes antegrade, epicardial injection, or infusion, of the left and right main coronary arteries. Also contemplated is retrograde injection or infusion of a coronary artery, or a combination of one or more antegrade and retrograde coronary arteries or veins.

Injection or infusion of one or more vasodilating substances, including but not limited to a NO increasing substance(s), into the coronary blood vessel(s) is performed using standard guide-wires, catheters and infusion pumps as needed. In a preferred embodiment, the injection or infusion catheter is directed to the coronary artery under fluoroscopic guidance via the femoral artery. As used herein, "blood vessel of the coronary circulation," "coronary blood vessel" or "blood vessel of the heart" includes grafts onto coronary blood vessels, for example those resulting from bypass surgery. As used herein, "epicardial" refers to blood vessels located on the outer portion of the heart, e.g. the left or right coronary arteries.

The amount of the vasodilating substance administered to the subject will depend on the size of the subject and the route of administration. In a preferred embodiment, the vasodilating substance or substances, including but not limited to a NO increasing substance or substances, is injected as a single bolus injection (typically in a volume of 0.1-2 mL, in less than a minute) directly into a coronary artery less than about 5 minutes prior to the administration of the viral vector or other therapeutic agent. In some embodiments, the vasodilator(s), including NO increasing substance(s), is administered locally or systemically, preferably by injection or infusion, at a time prior to the administration of the viral vector or therapeutic agent that is, is about, is at least, is at least about, is not more than, or is not more than about, 0.5, 1, 2, 3, 4, 5, 7, 10, 12, 15, 20, 25, or 30 minutes, 1, 2, 3 or more hours, or a range defined by any two of the preceding values. In a preferred embodiment, the range is 0.5-10 minutes. More preferably, the vasodilator(s) or NO increasing substance(s) is administered, preferably by a single bolus injection, immediately prior to the administration of the viral vector or therapeutic agent. In some embodiments, where the vasodilator(s) is administered by infusion, administration of the viral vector or therapeutic agent begins at a time following the end of the infusion of the vasodilator that is, is about, is at least, is at least about, is not more than, or is not more than about, 0.5, 1, 2, 3, 4, 5, 7, 10, 12, 15, 20, 25, or 30 minutes, 1, 2, 3 or more hours, or a range defined by any two of the preceding values.

In some embodiments, the vasodilator(s) or NO increasing substance(s) is injected or infused prior to the viral vector or therapeutic agent as described herein, and a second dose of the same or different vasodilator(s) or NO increasing substance(s) is administered concurrently with the viral vector or therapeutic agent, preferably over a period of at least 3 minutes, more preferably about 4 to about 10 minutes, or as described in more detail below. In other embodiments, no pretreatment with the vasodilator(s) or NO increasing substance(s) is given, and the vasodilator(s) is administered concurrently with the viral vector or therapeutic agent which is administered as described herein. In some embodiments, the concurrent administration is administration of the vasodilator in the same solution as the therapeutic agent. In other embodiments, the concurrent administration is via different routes of administration for the vasodilator and the therapeutic agent (e.g. intravenous and intracoronary, respectively).

In some embodiments, one or more vasodilator(s), including but not limited to NO increasing substance(s), are administered after the viral vector or therapeutic agent. This post-administration can be in addition to pretreatment and/or concurrent administration with the therapeutic substance, and can be the same or different vasodilator(s) as administered in the pretreatment and/or concurrent administration. In some embodiments, the vasodilator(s) or NO increasing substance(s) is administered, preferably by injection or infusion, at a time after the administration of the viral vector or therapeutic agent that is, is about, is at least, is at least about, is not more than, or is not more than about 0.5, 1, 2, 3, 4, 5, 7, 10, 12, 15, 20, 25, or 30 minutes, 1, 2, 3 or more hours, or a range defined by any two of the preceding values. In a preferred embodiment, the range is 0.5-10 minutes after administration of the viral vector.

In a preferred embodiment, the NO increasing substance is nitroglycerin, and the total amount of nitroglycerin administered via intracoronary injection or infusion, in one or more doses as described herein, is from about 50 µg to about 500 µg, more preferably from about 100 µg to about 150 µg. The contemplated total amount, or amount per dose, of nitroglycerin, or other vasodilator(s) or NO increasing substance(s), or combination of substances, administered via intracoronary injection or infusion is, is about, is at least, is at least about, is not more than, or is not more than about, 1, 2, 3, 4, 5, 7, 10, 12, 15, 20, 30, 40, 50, 60, 70, 80, 90, 100, 125, 150, 175, 200, 250, 300, 350, 400, 450, 500, 600, 700, 800, 900, or 1000 µg, or a range defined by any two of the preceding values. This amount can be the amount administered as a pretreatment, along with, or after the therapeutic agent, to a single coronary artery or all coronary arteries receiving an injection or infusion, or any combination thereof, or can be the total amount administered. One skilled in the art will appreciate that the dose of vasodilating agent used for intracoronary injection or infusion is relative to the size of the organ and not necessarily the subjects' total body weight. In one embodiment, an initial intracoronary injection of 50 µg of nitroglycerin is given prior to infusion of the viral vector, and a second amount of 100 µg of nitroglycerin is infused with the viral vector, preferably over at least 3 minutes, more preferably about 4 minutes, to about 10 minutes.

In some embodiments, the total dose of nitroglycerin administered systemically via intravenous injection or infusion is preferably from about 200 µg to about 4000 µg, more preferably from about 500 µg to about 2500 µg. The contemplated total dose of nitroglycerin administered via systemic injection or infusion is, is about, is at least, is at least about, is not more than, or is not more than about, 1, 2, 3, 4, 5, 7, 10, 12, 15, 20, 30, 40, 50, 60, 70, 80, 90, 100, 125, 150, 175, 200, 250, 300, 350, 400, 450, 500, 600, 700, 800, 900, 1000, 1250, 1500, 1750, 2000, 2250, 2500, 2750, 3000, 3500, or 4000 µg, or a range defined by any two of the preceding values. In some embodiments, nitroglycerin is administered intravenously, at or at about, 5 µg/minute, increased by 5 µg/minute every 3-5 minutes to 20 µg/minute; if there is no response at 20 µg/minute, the dose may be increased by 10 µg/minute every 3-5 minutes up to 200 µg/minute. The contemplated dose rates of nitroglycerin administered via systemic injection or infusion is, is about, is at least, is at least about, is not more than, or is not more than about, 1, 2, 3, 4, 5, 7, 10, 12, 15, 20, 30, 40, 50, 60, 70, 80, 90, 100, 125, 150, 175, 200, 250, 300, 350, or 400 µg/minute or a range defined by any two of the preceding values. The total time of infusion of the vasodilator(s) or NO increasing substance(s) is, is about, is at least, is at least about, is less than, is less than about, 5, 7, 10, 12, 15, 20, 25, 30, 35, 40, 45, 50, 55, 60, 65, 70, 75, 80, 85, 90, 95, 100, 110, 125, 150, 175, 200, 250, 300, 350, 400, 450, 500, or 600 minutes, or a range defined by any two of the preceding values. In some embodiments, IV infusion begins prior to, and continues during the administration of the viral vector or therapeutic agent.

In some embodiments, the total dose of nitroglycerin administered systemically by oral means is preferably from about 5 mg to about 105 mg, more preferably from about 10 mg to about 80 mg. In another embodiment, the preferred dose is about 15 mg to about 80 mg. The contemplated total dose of nitroglycerin administered orally is, is about, is at least, is at least about, is not more than, or is not more than about 0.4, 0.5, 0.75, 1, 2, 3, 4, 5, 7, 10, 12, 15, 20, 30, 40, 50, 60, 70, 80, 90, 100, or 125 mg, or a range defined by any two of the preceding values.

In another embodiment, the amount of nitroglycerin given systemically by sublingual administration is, is about, is at least, is at least about, is not more than, or is not more than about, 36, 54, 72, 90, 108, 126, 144, 162, 180, 198, 216, 234, 252, 270, 288, 306, 324, 342, or 360 mg or a range defined by any two of the preceding values. In some embodiments, nitroglycerin is administered sublingually where the dose is, is about, is at least, is at least about, is not more than, or is not more than about, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 mg, or a range defined by any two of the preceding values. The sublingual dose is administered at an interval that is, is about, is at least, is at least about, is not more than, or is not more than about, every 1, 2, 3, 4, 5, 6, 7, 8, 9, or 10 minutes or a range defined by any two of the preceding values. In a preferred embodiment, sublingual administration of nitroglycerin is given from about 0.2 to about 0.6 mg every 5 minutes for a maximum of 3 doses every 15 minutes. In another embodiment, nitroglycerin can be given translingually by spray, drops, or mist. One to 2 sprays into the mouth may be given every 3-5 minutes for a maximum of 3 doses in 15 minutes.

In some embodiments, systemic administration of nitroglycerin can be delivered transdermally with a transdermal patch. The total dose of nitroglycerin administered systemically via transdermal patch is preferably from about 2.4 mg to about 15.6 mg, more preferably from about 4.8 mg to about 9.6 mg. The contemplated total dose of nitroglycerin administered via a transdermal patch is, is about, is at least, is at least about, is not more than, or is not more than about, 2.4, 3.6, 4.8, 6, 7.2, 8.4, 9.6, 10.8, 12, 13.2, 14.4, or 15.6 mg, or a range defined by any two of the preceding values. In some embodiments, nitroglycerin is administered by a transdermal patch where the dose is, is about, is at least, is at least about, is not more than, or is not more than about 0.1, 0.15, 0.2, 0.25, 0.3, 0.35, 0.4, 0.45, 0.5, 0.55, 0.6, or 0.65 mg, or a range defined by any two of the preceding values. The transdermal patch dose is administered at an interval that is, is about, is at least, is at least about, is not more than, or is not more than about, every 15, 30, 45, 60, 75, or 90 minutes or a range defined by any two of the preceding values. In another embodiment, the contemplated dose rates of nitroglycerin administered via a transdermal patch is, is about, is at least, is at least about, is not more than, or is not more than about, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 mg/hour, or a range defined by any two of the preceding values. In a preferred embodiment, nitroglycerin is given transdermally at an initial dose of about 0.2-0.4 mg/hour, up to doses of 0.4-0.8 mg/hour. Tolerance is minimized by using a patch-on period of 12-14 hours and a patch-off period of about 10-12 hours.

In another embodiment, systemic administration of nitroglycerin can be delivered transdermally by topical application of an ointment. The contemplated total dose of nitroglycerin administered via topical ointment is, is about, is at least ½" square inch upon rising and ½" square inch 6 hours later at a concentration of, or of about 0.1%, 0.15%, 0.2%, 0.25%, 0.3%, 0.4%, 1%, or 2% nitroglycerin, or a range defined by any two of the preceding values. In preferred embodiment, the concentration of the ointment is 0.2%. The dose may be doubled several times as needed.

Some embodiments contemplate systemic delivery of nitroglycerin through the skin by subcutaneous injection or infusion. In some embodiments, the total dose of nitroglycerin administered subcutaneously is preferably from about 5 mg to about 105 mg, more preferably from about 10 to about 80 mg. In another embodiment, the preferred dose is about 15 mg to about 80 mg. The contemplated total dose of nitroglycerin administered subcutaneously is, is about, is at least, is at least about, is not more than, or is not more than about 0.4, 0.5, 0.75, 1, 2, 3, 4, 5, 7, 10, 12, 15, 20, 30, 40, 50, 60, 70, 80, 90, 100, or 125 mg, or a range defined by any two of the preceding values.

In a preferred embodiment, the vasodilator(s) or NO increasing substance(s) or combination of substances is administered without any other vasodilator or vascular permeation enhancing substance in an amount sufficient to increase vasodilatation or vascular permeability. In some embodiments, the NO increasing substance or combination of substances, preferably nitroglycerin, is the only vasodilator or vascular permeation enhancer administered before, during and/or after the administration of the viral vector or therapeutic agent. In some embodiments, no vasodilator or vascular permeation enhancing substance is administered before, during and/or after the administration of the viral vector or therapeutic agent, other than the NO increasing substances described herein. In an embodiment, the subject is not treated with any vasodilator or permeation enhancing substance in an amount sufficient to enhance the uptake of a viral vector or therapeutic agent, before, during and/or after the administration of the viral vector or therapeutic agent, other than the NO increasing substances described herein, preferably nitroglycerin. Vasodilatory or permeation enhancing substances which are preferably excluded from administration in some embodiments include, but are not limited to, vascular endothelial growth factor (VEGF), adenosine and calcium.

In some embodiments, the amount of vasodilator substance or substances is a transfection enhancing or pharmaceutically or therapeutically effective amount, wherein the amount is sufficient to enhance the efficiency of transduction of the viral vector or therapeutic agent. The enhancement of transfection can be directly measured by examining transfection efficiency, or indirectly, by measuring other indicators of successful transfection such as improvements in one or more symptoms or outcomes discussed herein. An enhancing amount is an amount that improves the indicator examined in comparison to the same indicator when the vasodilator(s) or NO increasing substance(s) is not administered.

Therapeutic Agent Administration

In a preferred embodiment of the invention, the therapeutic agent, e.g. polynucleotide/viral vector described in more detail below, is administered to the subject by infusion into a blood vessel of the coronary circulation of the beating heart in vivo for a period of at least about three minutes in a particular blood vessel. In large animal models of the human heart and cardiovascular disease, Applicant has found that, unexpectedly, for administration of viral vectors a relatively long infusion time is more effective and results in superior gene transfer efficiency into heart tissue than a bolus injection or short (e.g., $\leq 1$ minute) infusion time of the same amount of viral vector. The improved efficacy of infusion can be measured as a greater copy number of the transgene per cell, increased expression of the transgene at the mRNA and/or protein level per cell or in the tissue, and/or a greater percentage of cells of a particular tissue, e.g. cardiomyocytes, being transfected, as compared to injection. In another embodiment, clinical or functional measurements may be used to demonstrate the transfection efficiency from a relatively long infusion time. Such clinical and functional assessments are described further herein.

Applicant has shown that this method results in successful treatment of large animal models of human cardiovascular disease. In addition, Applicant has discovered that by using relatively long infusion times, there is no need to isolate the coronary circulation from the systemic circulation or otherwise re-circulate the therapeutic agent, or to artificially restrict the coronary venous circulation as a means to increase pressure within the coronary circulation or to increase dwell time of the therapeutic agent. Nor is there any need to cool the heart, stop the heart, or remove the heart from the animal for perfusion. Instead, Applicant's method can be practiced in a standard catheterization lab setting using existing catheters for administration. Thus, Applicant has discovered a simple, practical, and efficacious means of using gene therapy to treat cardiovascular disease in large animals, such as humans.

In a preferred embodiment of the invention, the therapeutic agent is administered to the subject by infusion into a blood vessel of the coronary circulation. The coronary circulation provides blood supply to the tissue of the heart. There are a number of coronary arteries. Normally, four main coronary arteries provide oxygenated blood to the heart for distribution throughout the heart tissue; the left main and right coronary arteries, the left anterior descending artery, and the left circumflex artery. Infusion of one or a combination of these arteries is contemplated, for example infusion of the left and right coronary arteries. The preferred embodiment utilizes antegrade, epicardial infusion of the left and right main coronary arteries. Also contemplated is retrograde infusion of a coronary artery, or a combination of one or more antegrade and retrograde coronary arteries or veins. Infusion of the coronary blood vessel(s) is performed using standard guidewires, catheters and infusion pumps. In a preferred embodiment, the infusion catheter is directed to the coronary artery under fluoroscopic guidance via the femoral artery. As used herein, "blood vessel of the coronary circulation," "coronary blood vessel" or "blood vessel of the heart" includes grafts onto coronary blood vessels, for example those resulting from bypass surgery. As used herein, "epicardial" refers to blood vessels located on the outer portion of the heart, e.g. the left or right coronary arteries.

Once the infusion catheter is in place in the target coronary blood vessel, the therapeutic agent is infused into the blood vessel, preferably by means of a programmable infusion pump. The amount of time taken to infuse the therapeutic agent is an important factor in obtaining effective and superior gene transfer efficiency. Applicant has determined that an infusion time of at least about 3 minutes into a particular blood vessel is more effective than a bolus injection or shorter infusion time. Preferably, the infusion time is at least about 8 minutes, more preferably at least about 10 minutes, although infusion times of at least about 15 minutes are contemplated. Applicant also contemplates that the infusion time is, is about, is at least, is at least about, is not more than, or is not more than about, 1, 2, 3, 4, 5, 6, 7, 8, 9, 10, 11, 12, 13, 14, 15, 16, 17, 18, 19, or 20 minutes, or falls within a range defined by any two of these values.

Because the infusion typically involves the use of a catheter and connecting tubing which has a certain dead volume, the infusion device is often primed with a carrier solution, e.g. blood from the subject, which does not contain any therapeutic agent. Thus, the therapeutic agent is not immediately administered into the coronary circulation when the infusion pump is turned on. Likewise, when the syringe containing the therapeutic agent is emptied, an amount of therapeutic agent typically remains in the dead volume of the connecting tubing and catheter. Immediately following the infusion of the therapeutic agent, the dead volume is flushed with an appropriate solution. The period of time over which the therapeutic agent is actually being delivered into the coronary circulation, as opposed to displacing dead volume in the infusion apparatus, is the "infusion time" referred to above. For example, if 3 mL of therapeutic agent is loaded into an infusion apparatus with 3 mL of dead volume, and the infusion rate is 1 mL/min., the time required to infuse the therapeutic agent into the coronary circulation is only 3 minutes, while the total time required to administer the 3 mL of therapeutic agent and 3 mL of dead volume is 6 minutes. In some embodiments, the catheter and any connecting tubing is primed with the therapeutic agent such that the dead volume is not an issue. Similarly, the effective amount of therapeutic agent could be delivered without the need to flush the tubing. However, this results in therapeutic agent being left in the tubing, wasting the therapeutic agent.

Applicant contemplates that the therapeutic agent will be infused at a flow rate that is, is about, is at least, is at least about, is not more than, or is not more than about, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5, or 10.0 mL/min., or falls within a range defined by any two of these values. Preferably, the flow rate is between about 0.2 mL/min and about 6.0 mL/min., more preferably between about 0.2 mL/min and about 2.5 mL/min., more preferably between about 0.2 mL/min. and about 2.0 mL/min. Those of skill in the art will recognize that delivery of the therapeutic agent is possible without an infusion pump, however more accurate flow rates and uniform delivery are possible with the use of an infusion pump.

The total amount of viral particles or DNase resistant particles (DRP) delivered by infusion to provide an effective amount is preferably between $1 \times 10^{14}$ and about $1 \times 10^{11}$, more preferably between about $3 \times 10^{12}$ and $1 \times 10^{12}$, and more preferably about $3 \times 10^{12}$. However, applicant also contemplates that the total amount of viral particles or DRP is, is about, is at least, is at least about, is not more than, or is not more than about, $1 \times 10^{14}$, $9 \times 10^{13}$, $8 \times 10^{13}$, $7 \times 10^{13}$, $6 \times 10^{13}$, $5 \times 10^{13}$, $4 \times 10^{13}$, $3 \times 10^{13}$, $2 \times 10^{13}$, $1 \times 10^{13}$, $9 \times 10^{12}$, $8 \times 10^{12}$, $7 \times 10^{12}$, $6 \times 10^{12}$, $5 \times 10^{12}$, $4 \times 10^{12}$, $3 \times 10^{12}$, $2 \times 10^{12}$, $1 \times 10^{12}$, $9 \times 10^{11}$, $8 \times 10^{11}$, $7 \times 10^{11}$, $6 \times 10^{11}$, $5 \times 10^{11}$, $4 \times 10^{11}$, $3 \times 10^{11}$, $2 \times 10^{11}$, $1 \times 10^{11}$, $9 \times 10^{10}$, $8 \times 10^{10}$, $7 \times 10^{10}$, $6 \times 10^{10}$, $5 \times 10^{10}$, $4 \times 10^{10}$, $3 \times 10^{10}$, $2 \times 10^{10}$, $1 \times 10^{10}$, $9 \times 10^{9}$, $8 \times 10^{9}$, $7 \times 10^{9}$, $6 \times 10^{9}$, $5 \times 10^{9}$, $4 \times 10^{9}$, $3 \times 10^{9}$, $2 \times 10^{9}$, $1 \times 10^{9}$, or falls within a range defined by any two of these values.

The number of DRP infused over a given time is a function of the concentration of the solution being infused and the flow rate. The rate of DRP or viral particle infusion is preferably between about $1 \times 10^{8}$/min. and about $1 \times 10^{14}$/min., more preferably between about $5 \times 10^{10}$/min. and about $5 \times 10^{12}$/min., more preferably between about $3 \times 10^{10}$/min. and about $1 \times 10^{12}$/min., more preferably between about $6 \times 10^{10}$/min. and about $4 \times 10^{11}$/min. In a preferred embodiment, the rate of DRP or viral particle infusion is $1 \times 10^{11}$/min., and in another preferred embodiment, it is $1.25 \times 10^{11}$/min.

In one embodiment, the therapeutic agent is administered into a single blood vessel of the heart. In another embodiment ⅔ of the total volume of therapeutic agent is delivered to one blood vessel of the heart, and ⅓ is administered to another blood vessel of the heart. In another embodiment, more than 2 coronary blood vessels are infused, (e.g. 3, 4, 5 or more), and the portion of total infusion volume containing the therapeutic agent administered per blood vessel can be adjusted as appropriate. The goal of the infusion is to provide diffuse, homogenous left ventricular myocardial exposure to AAV2/1/SERCA2a via anterograde, epicardial coronary infusion. Multiple infusion scenarios exist based on collateralization patterns, occlusive disease, and anatomic variation (e.g. post surgical bypass anatomy), but the clinician's goal is ⅓ of AAV2/1/SERCA2a delivered to the anterolateral, ⅓ delivered to the posterolateral, and ⅓ delivered to the inferior/inferolateral myocardium. Anatomy is defined by coronary and bypass graft angiography to accomplish homogenous delivery to the perfused myocardium. In addition, one of skill in the art will recognize that while sheep and pigs are accepted animal models for human cardiovascular studies, sheep and pigs are 90% left dominant. In comparison, approximately ~10% of the human population is left dominant, with the remaining 90% being right or co-dominant (Vlodaver Z. et al. Coronary Heart Disease: Clinical, Angiographic, and Pathologic Profiles. Spinger-Verlag, New York. 1976). One pathologic series suggests that 71% of patients are right dominant, 17% co-dominant, 12% are left dominant (McAlpine W. Heart and Coronary Arteries. Spinger Verlag, 1975). Therefore, to achieve a similar perfusion of the left ventricle in humans vs. pigs/sheep, the optimum infusion scenario can differ.

A ⅓ and ⅔ split of the solution volume is preferred for two blood vessels, however the portion of the injection volume infused into a particular blood vessel can be a volume that is, is about, is at least, is at least about, is not more than, or is not more than about, 20, 25, 30, 35, 40, 45, 50, 55, 60, 65, 70, 75, or 80% of the total volume, or falls within a range defined by any two of these values. The total volume of solution containing the therapeutic agent will vary according to the size of the animal being treated. For a human subject, a total therapeutic agent volume of 60 mL is preferred. However the total volume of therapeutic agent can be a volume that is, is about, is at least, is at least about, is not more than, or is not more than about, 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, or 150 mL, or falls within a range defined by any two of these values.

The therapeutic agents described herein can be in solution, preferably a pharmaceutical composition suitable for administration directly into the coronary circulation. The ingredients of an acceptable pharmaceutical composition are known to those of skill in the art, and can include such elements as a buffer and suitable carrier. In another embodiment, the pharmaceutical composition containing a therapeutic agent, for example a viral vector, and more preferably a AAV2/1/SERCA2a vector, is part of a kit. In some embodiments, the kit contains a stock solution of therapeutic agent and a solution for diluting the stock solution. Also included in the kit are instructions for administration of the viral vector, preferably by infusion directly into the coronary circulation as described in any of the embodiments disclosed herein. The therapeutic agents and vasodilator(s), including but not limited to NO increasing substance(s), described herein can be used in the manufacture of a medicament for the treatment of the diseases disclosed herein, where the medicament is administered according to or in the practice of any of the methods disclosed herein.

Methods of Polynucleotide Delivery

One aspect of the present invention contemplates transfer of therapeutic polynucleotides into a cell. Such transfer may employ viral or non-viral methods of gene transfer. This section provides a discussion of methods and compositions of gene or nucleic acid transfer, including transfer of antisense, interfering, and small interfering sequences.

In one embodiment, the therapeutically significant polynucleotides are incorporated into a viral vector to mediate transfer to a cell. Additional expression constructs encoding other therapeutic agents as described herein may also be transferred via viral transduction using infectious viral particles, for example, by transformation with an adeno-associated virus (AAV) or AAV molecular variants of the present invention. Alternatively, a retrovirus, bovine papilloma virus, an adenovirus vector, a lentiviral vector, a vaccinia virus, a polyoma virus, or an infective virus that has been engineered to express may be used. Similarly, nonviral methods which include, but are not limited to, direct delivery of DNA such as by perfusion, naked DNA transfection, liposome mediated transfection, encapsulation, and receptor-mediated endocytosis may be employed. These techniques are well know to those of skill in the art, and the particulars thereof do not lie at the crux of the present invention and are thus need not be exhaustively detailed herein. However, in one preferred example, a viral vector is used for the transduction of cardiac cells to deliver a therapeutically significant polynucleotide to a cell. The virus may gain access to the interior of the cell by a specific means such receptor-mediated endocytosis, or by non-specific means such as pinocytosis.

Adeno-associated Virus Vectors

A preferred embodiment of the invention utilizes purified, replication incompetent, pseudotyped recombinant adeno-associated viral (rAAV) particles. Adeno-associated viruses (AAV) are parvoviruses belonging to the genus *Dependovirus*. They are small, nonenveloped, single-stranded DNA viruses which require a helper virus in order to replicate. Co-infection with a helper virus (e.g., adenovirus, herpes virus, or vaccinia virus) is necessary in order to form functionally complete AAV virions. In vitro, in the absence of co-infection with a helper virus, AAV establishes a latent state in which the viral genome exists in an episomal form, but infectious virions are not produced. Subsequent infection by a helper virus "rescues" the genome, allowing it to be replicated and packaged into viral capsids, thereby reconstituting the infectious virion. Recent data indicate that in vivo both wild type AAV and recombinant AAV predominantly exist as large episomal concatemers.

AAV are not associated with any known human diseases, are generally not considered pathogenic, and do not appear to alter the physiological properties of the host cell upon integration. AAV can infect a wide range of host cells, including non-dividing cells, and can infect cells from different species. In contrast to some vectors, which are quickly cleared or inactivated by both cellular and humoral responses, AAV vectors have shown persistent expression in various tissues in vivo. The persistence of recombinant AAV vectors in non-diving cells in vivo may be attributed to the lack of native AAV viral genes and the vector's ability to form episomal concatemers.

Adeno-associated virus (AAV) is an attractive vector system for use in cell transduction because it has a high frequency of persistence as an episomal concatemer and it can infect non-dividing cells, thus making it useful for delivery of genes into mammalian cells, for example, in tissue culture and in vivo. Studies demonstrating the use of AAV in gene delivery include Flotte et al, Proc. Natl. Acad. Sci. USA, 1993; 90:10613-17 and Walsh et al., J. Clin. Invest., 1994; 94:1440-48. Recombinant AAV vectors have been used successfully for in vitro and in vivo transduction of marker genes and genes involved in human diseases (see for example, Walsh et al., J. Clin. Invest. 1994; 94:1440-48). AAV has a broad host range for infectivity. Details concerning the generation and use of rAAV vectors are described in U.S. Pat. Nos. 5,139,941 and/or 4,797,368, each incorporated herein by reference.

Typically, recombinant AAV (rAAV) virus is made by cotransfecting a plasmid containing the gene of interest flanked by the two AAV terminal repeats and/or an expression plasmid containing the wild-type AAV coding sequences without the terminal repeats, for example pIM45. The cells are also infected and/or transfected with adenovirus and/or plasmids carrying the adenovirus genes required for AAV helper function. rAAV virus stocks made in such fashion are contaminated with adenovirus which must be physically separated from the rAAV particles (for example, by cesium chloride density centrifugation or column chromatography). Alternatively, adenovirus vectors containing the AAV coding regions and/or cell lines containing the AAV coding regions and/or some or all of the adenovirus helper genes could be used. Cell lines carrying the rAAV DNA as an integrated provirus can also be used.

Multiple serotypes of AAV exist in nature, with at least twelve serotypes (AAV1-AAV12) currently known. Moreover, chimeric variants have been produced through directed evolution (DNA shuffling) technology (see Li et al.). Despite the high degree of homology, the different serotypes have tropisms for different tissues. The receptor for AAV1 is unknown; however, AAV1 is known to transduce skeletal and cardiac muscle more efficiently than AAV2. Since most of the studies have been done with pseudotyped vectors, in which the vector DNA flanked with AAV2 ITR is packaged into capsids of alternate serotypes, it is clear that the biological differences are related to the capsid rather than to the genomes. Recent evidence indicates that DNA expression cassettes packaged in AAV1 capsids are at least 1 $\log_{10}$ more efficient at transducing cardiomyocytes than those packaged in AAV2 capsids.

Engineered rAAV Vectors

In one embodiment, AAV vectors can be engineered to reduce neutralizing antibody (NAb) titers and/or cross-reactivity. Preferably, the cross-reactivity of the engineered or chimeric vector with a Nab is at least 50, 55, 60, 65, 70, 75, 80, 85, 90, 95, 97, or 99% less than the cross-reactivity of wild-type vector. More preferably, the cross-reactivity is essentially absent. Reducing cross-reactivity and/or NAb titers may be carried out by engineering AAV capsid proteins to create chimeric and/or altered rAAV vectors. Several methods are known in the art to engineer genes, e.g., capsid genes, including, but not limited to, DNA shuffling (family or single gene) (see Li et al., Crameri, A et al. (1998). "DNA shuffling of a family of genes from diverse species accelerates directed evolution." Nature 391:288-291, and Stemmer, W P (1994). "Rapid evolution of a protein in vitro by DNA shuffling." Nature 370: 389-391, all hereby incorporated by reference in their entirety), site-directed mutagenesis, error-prone PCR (Moore, G. L., Maranas, C. D., 2000. "Modeling DNA mutation and recombination for directed evolution experiments." J. Theor. Biol. 205, 483-503, incorporated herein by reference), generating chimeras, or combinations thereof such as a staggered extension process which is a method that incorporates DNA shuffling and error-prone PCR techniques (Maheshri, N et al. (2006). "Directed evolution of adeno-associated virus yields enhanced gene delivery vectors." Nat Biotechnol 24:198-204, herein incorporated by reference in its entirety). Once the capsid proteins undergo engineering, rAAV vectors are assayed for the desirable properties for which one is selecting or screening. For example, selections and/or screens may be used to isolate rAAV clones that have incorporated properties that produce a reduction in reactivity or cross-reactivity to NAbs. As described in Li et al., altered rAAV vectors were produced after using the DNA shuffling technique on the genes responsible for encoding the AAV capsid proteins (i.e., the cap genes). The engineered rAAV clone that the authors created was produced from a combination of multiple serotypes and thus contained genomic fragments representing various parental serotypes. In order to assess the immunological profile of the altered rAAV vector, it was subjected to a series of crossreactivity tests. In these tests, antisera was taken from mice that were immunized with a particular AAV serotype (i.e., a parental serotype) from which the engineered rAAV vector was derived. The assays, in the Li et al. study, assessed the NAb titers and the extent to which the engineered rAAV vector cross-reacted with antisera generated from mice that were immunized with the AAV parental serotypes. Results showed that antisera from 3 of the 4 parental serotypes did not cross-react with the engineered rAAV clone while the remaining sample showed a 25-fold lower NAb titer.

In another embodiment, AAV vectors can be engineered for increased transduction efficiency and/or specificity. Increasing transduction efficiency and/or specificity may be carried out by engineering AAV capsid proteins to create chimeric and/or altered rAAV vectors. Several methods are known in the art to engineer genes including, but not limited to, DNA shuffling (family or single gene), site-directed mutagenesis, error-prone PCR, generating chimeras, or combinations hereof such as a staggered extension process which is a technique that incorporates DNA shuffling and error-prone PCR. Once the capsid proteins undergo engineering, rAAV vectors are assayed for the desirable properties for which one is assaying. For example, selections and/or screens may be used to isolate rAAV variants that have been endowed with an increase in efficiency and/or specificity for the targeted tissue(s) or cells.

Therapeutic Effect

In a preferred embodiment, the infusion of the therapeutic agents disclosed herein are used to achieve a therapeutic effect in a patient suffering from cardiac disease. The treated individual may be monitored for clinical features which accompany the cardiac disorder to determine if a therapeutic effect is achieved. For example, subjects may be monitored for reduction in adverse signs and symptoms associated with cardiovascular disease. For example, after treatment of congestive heart failure in a subject using methods disclosed herein, the subject may be assessed for improvements in a number of parameters including, but not limited to, increased lateral ventricle fractional shortening, augmented cardiac contractility at the cellular and intact animal levels, reversal of cardiac remodeling, and normalization of the abnormally high diastolic levels of cytosolic calcium. Other clinical and cardiac parameters which can be monitored in a subject treated with the present technology include without limitation survival, cardiac metabolism, heart contractility, heart rate, ventricular function (e.g., left ventricular end-diastolic pressure (LVEDP), left ventricular systolic pressure (LVSP)), $Ca^{2+}$ metabolism (e.g., intracellular $Ca^{2+}$ concentration, peak or resting $[Ca^{2+}]$, SR $Ca^{2+}$ ATPase activity, phosphorylation state of phospholamban), force generation, relaxation, a force-frequency relationship, cardiomyocyte survival or apoptosis or ion channel activity (e.g., sodium calcium exchange, sodium channel activity, calcium channel activity, sodium potassium ATPase pump activity), activity of myosin heavy chain, BNP and NT-proBNP, troponin I, troponin C, troponin T, CK-MB, tropomyosin, actin, myosin light chain kinase, myosin light chain 1, myosin light chain 2 or myosin light chain 3, IGF-1 receptor, PI3 kinase, AKT kinase, sodium-calcium exchanger, calcium channel (L and T), calsequestrin, or calreticulin. The evaluation can be performed before, after, and during the treatment. Other measures of cardiac disease which can be monitored include fractional shortening, cardiac output, ejection fraction, Tau, regurgitant volume, number of hospital stays, quality of life, and treadmill time, distance walked during 6 minute walk test, and maximal oxygen consumption ($VO_2$max). In one embodiment, patients may be monitored with molecular biological techniques known in the art to measure the rAAV vector DNA, RNA, and/or proteins present in the cells and/or tissues. In some embodiments, one can assess the copy number of the transgene per cell, the expression of the transgene at the mRNA and/or protein level per cell or in the tissue, and/or the percentage of cells of a particular tissue, e.g. cardiomyocytes, being transfected.

In a preferred embodiment, the administration of a vasodilating substance, preferably a NO increasing substance as described herein, more preferably nitroglycerin, increases the efficiency of transduction of the therapeutic agent. In some embodiments, the administration of a vasodilator or NO increasing substance improves the therapeutic effect achieved by administration of the therapeutic agent alone, wherein the therapeutic effect is monitored as described herein. In some embodiments, the administration of a vasodilator or NO increasing substance results in improved efficacy of the therapeutic agent, such that the same level of therapeutic effect can be achieved with less therapeutic agent. The improved efficacy can result in less therapeutic agent being needed in a single administration, or in fewer administrations of the therapeutic agent over time. In some embodiments, the administration of a vasodilating substance improves the therapeutic effect achieved by administration of the therapeutic agent alone by increasing the duration of the therapeutic effect. In some embodiments, the improvement in the transduction efficiency, therapeutic effect, or efficacy of the therapeutic agent is, is about, is at least, is at least about, 5, 10, 15, 20, 25, 30, 35, 40, 45, 50, 55, 60, 65, 70, 75, 80, 90, 100, 125, 150, 175, or 200%, or 2, 3, 4, 5, 7, 10, 15, or 20 times, or a range defined by any two of the preceding values, when compared to the value achieved without the administration of the vasodilating substance. For example, if an increase in ejection fraction is observed to last for 3 months following treatment without the vasodilator, a 50% increase in the therapeutic effect following treatment with the vasodilator would result in an increase in ejection fraction that lasts for 4.5 months.

The disclosed methods and therapeutic agents disclosed herein can be combined with existing treatments for cardiac disease, such as drugs or surgical intervention, to provide an enhanced therapeutic effect compared to existing treatments alone. An enhanced therapeutic effect may be demonstrated by, for example, an extension of the time period between the worsening of the signs or symptoms of the disease compared to the average or typical time period for existing treatment regimens, or the lengthening of time required before additional treatment is required compared to the average or typical time for standard treatment alone.

Kits

Other embodiments contemplated herein are kits comprising a container of a therapeutic agent, for example a viral vector, and more preferably a AAV2/1/SERCA2a vector, and a container of a vasodilating substance or substances. In some embodiments, the kit contains a stock amount of therapeutic agent and a carrier solution for dissolving or diluting the stock amount. In some embodiments, the kit contains a stock amount of the vasodilator(s), including but not limited to NO increasing substance(s), and a carrier solution for dissolving or diluting the stock amount. In some embodiments, the kit contains a container with a mixture of the therapeutic agent and the amount of vasodilating substance(s). The stock amounts of the therapeutic agent and/or vasodilating substance(s) can be in dry form requiring dissolution or mixing in a carrier solution, a concentrated solution requiring dilution, or in a form ready for administration to the patient without additional preparation. In some embodiments, the kit includes one or more intravascular infusion or injection catheters for intracoronary administration of the vasodilating substance(s) and/or therapeutic agent. In some embodiments, the kit includes one or more devices for administration of the compounds in the kit through the catheter, for example, a syringe. The kit can also include instructions for administration of the viral vector and/or therapeutic agent, as described in any of the embodiments disclosed herein, preferably by infusion directly into the coronary circulation.

Embodiments of the invention will now be further described in the following non-limiting examples. All references disclosed herein, including patents and non-patent literature, are hereby incorporated by reference in their entirety, and specifically for the disclosure thereof mentioned herein.

EXAMPLE 1

A 30 Day, Single Dose, Tissue Distribution Study of Direct Intracoronary Infusion of AAV1/SERCA2a (MYDICAR(®) in Normal Göttingen Minipigs

| I. PROTOCOL SYNOPSIS Protocol Synopsis | |
|---|---|
| Title: | A 30 Day, Single Dose, Tissue Distribution Study of Direct Intracoronary Infusion of AAV1/SERCA2a (MYDICAR ®) in Normal Göttingen Minipigs |
| Purpose: | To demonstrate the effect of pre-treatment with vasodilating agents such as nitroglycerin on AAV1/SERCA2a persistence in cardiac tissue at 30 days following a single administration of AAV1/SERCA2a (MYDICAR ®) in Göttingen minipigs with <1:2 baseline titer of anti-AAV1 neutralizing antibodies |
| Study Design | See Table 1 below |
| Animal Model, Species & Sex: | Normal male and female Göttingen minipigs |
| Test Product: | Vehicle control (CEL-1 formulation buffer) AAV1/SERCA2a test article |
| Dosage: | $10^{13}$ DRP AAV1/SERCA2a total dose ($\approx 10^{12}$ DRP/kg); Normal saline control |
| Route of Administration: | AAV1/SERCA2a: Antegrade epicardial coronary artery infusion Nitroglycerin Administration Group 3: 50 µg nitroglycerin was administered as a bolus intracoronary injection immediately prior to administration of AAV1/SERCA2a (see below "Method of Administration") Nitroglycerin Administration Group 4: 50 µg nitroglycerin was administered as a bolus intracoronary injection immediately prior to administration of AAV1/SERCA2a, and 100 µg nitroglycerin was also co-administered with AAV1/SERCA2a No other permeability enhancers are administered to any group (see below "Method of Administration") |
| Total Sample Size: | 26 animals total (see Table 1) |
| Study Duration: | 30 days total: dosing on Day 0, sacrifice at 30 days post-dosing |
| Assessments: | The following assessments were performed: During infusion: Vital signs and hemodynamic monitoring (blood pressure, heart rate and rhythm, respiratory rate, and O2 pulse oximeter, and end-tidal carbon dioxide). Hematology/coagulation parameters Clinical chemistry parameters Cardiac enzymes (creatine kinase (CK) (total and isoenzymes BB, MB, and MM) and troponin I) AAV1 neutralizing antibody pre-screening Expression of SERCA2a in cardiac tissue via RT-PCR and Western blot Body and organ weights Gross or macroscopic findings |
| Expression of SERCA2a: | SERCA2a mRNA expression was assessed via RT-PCR in the heart (12 regions) at terminal sacrifice on Day 30 SERCA2a protein expression was assessed via western blot in the heart (12 regions) at terminal sacrifice on Day 30 in three animals from Group 1, three animals from Group 3, and one animal from Group 5. |

TABLE 1

| | | Group Designation and Dose Levels | | | | |
|---|---|---|---|---|---|---|
| Treatment Group | Total | Nitroglycerin Pre-Treat (µg) | Nitroglycerin Co-Admin (µg) | Infusion Duration (min) | Test Article | Saline Control |
| Group #1 No nitroglycerin pre-treatment/ AAV1/SERCA2a 10 min infusion | 6 | No | No | 10 | ✓ | |
| Group #2 No nitroglycerin pre-treatment/ AAV1/SERCA2a 4 min infusion | 6 | No | No | 4 | ✓ | |
| Group #3 Pre-treat 50 µg nitroglycerin/ AAV1/SERCA2a 10 min infusion | 6 | 50 | No | 10 | ✓ | |
| Group #4 Pre-treat 50 µg nitroglycerin/ AAV1/SERCA2a + 100 µg nitroglycerin 10 min infusion | 6 | 50 | 100 | 10 | ✓ | |
| Group #5 No nitroglycerin pre-treatment/ Saline Control 10 min infusion | 2 | No | No | 10 | | ✓ |

Method of Administration

Administration on Day 0 was via the direct coronary infusion procedure described below. Animals from Groups 1-3 were dosed with a total volume of 12 mL of AAV1/SERCA2a solution which was infused at a constant rate of 1.2 mL/minute over a 10 minute period. Animals from Groups 3 and 4 received nitroglycerin as a bolus intracoronary injection immediately prior to administration of AAV1/SERCA2a. Animals from Group 3 were dosed with a total volume of 12 mL of AAV1/SERCA2a and nitroglycerin solution, which was infused at a constant rate of 1.2 mL/minute over a 10 minute period. Animals from Group 4 were dosed with a total volume of 12 mL of normal saline, which was infused at a constant rate of 1.2 mL/minute over a 10 minute period. The direct infusion system is composed of standard (commercially available) components including a conventional guide sheath, 0.014" guide-wire, a 5F infusion (guide) catheter and two programmable syringe pumps. The direct intracoronary infusion procedure began with introduction of the conventional guide sheath using a common carotid arterial or femoral arterial approach. The Coronary Infusion Catheter (e.g., Cordis Vista Brite Tip Guiding Catheter or similar model appropriate for cannulation of the left main coronary artery) was then placed in the left main coronary artery under fluoroscopic guidance. Once the catheter was in place, it was connected to the first programmable syringe pump (e.g., NE-1000 Programmable Syringe Pump, New Era Pump Systems) using standard tubing and purging technique. The AAV1/SERCA2a was then delivered, followed by a sterile saline flush of the catheter dead volume with the second programmable syringe pump.

Results

Figure 2:
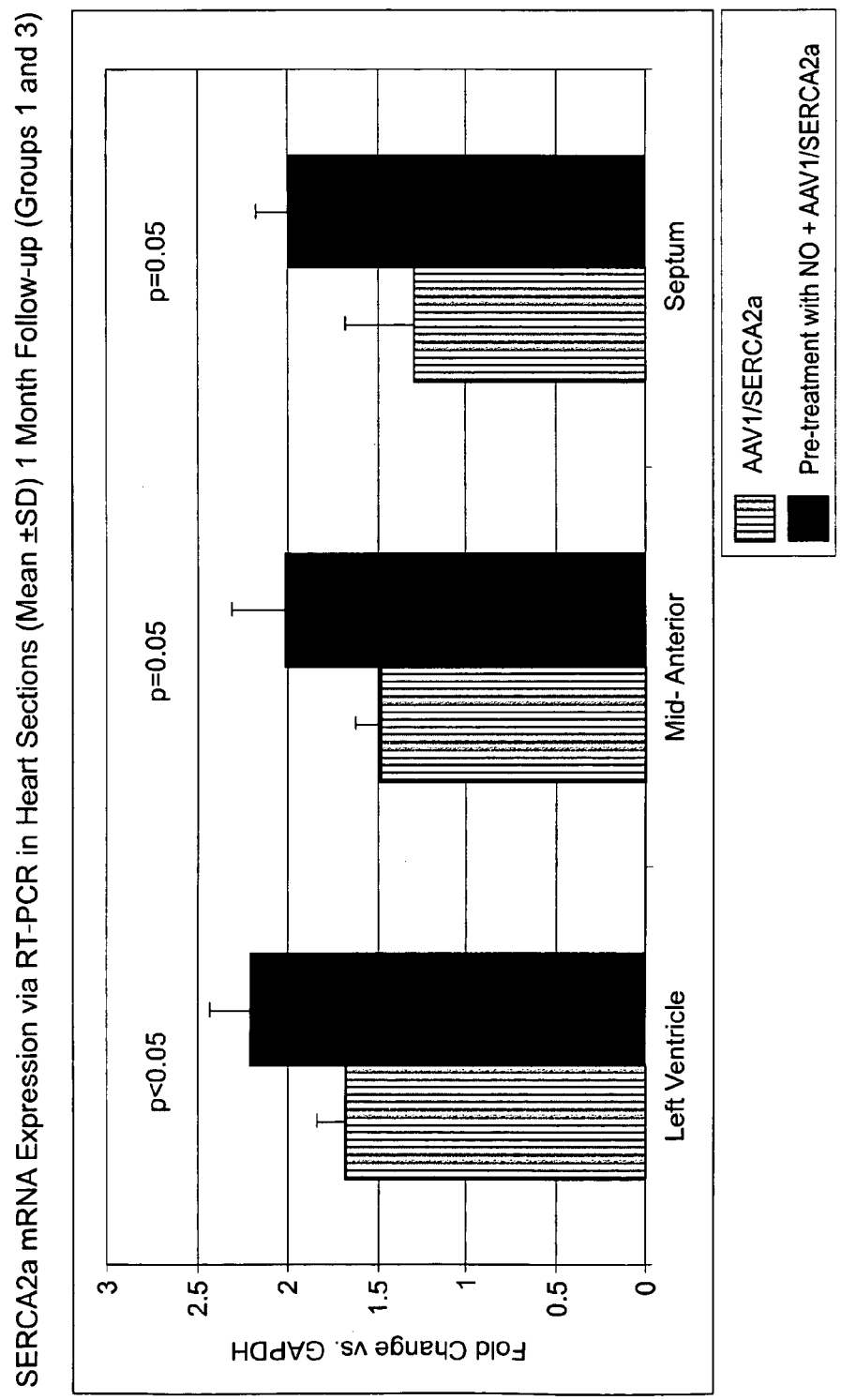
FIG. 2. Results from a 30 day, single dose, cardiac distribution study of direct intracoronary infusion of AAV1/SERCA2a in normal Göttingen Minipigs. Graphs demonstrate SERCA2a mRNA expression via RT-PCR in heart sections at a 1-month of follow-up from Groups 1 and 3.
Figure 3:
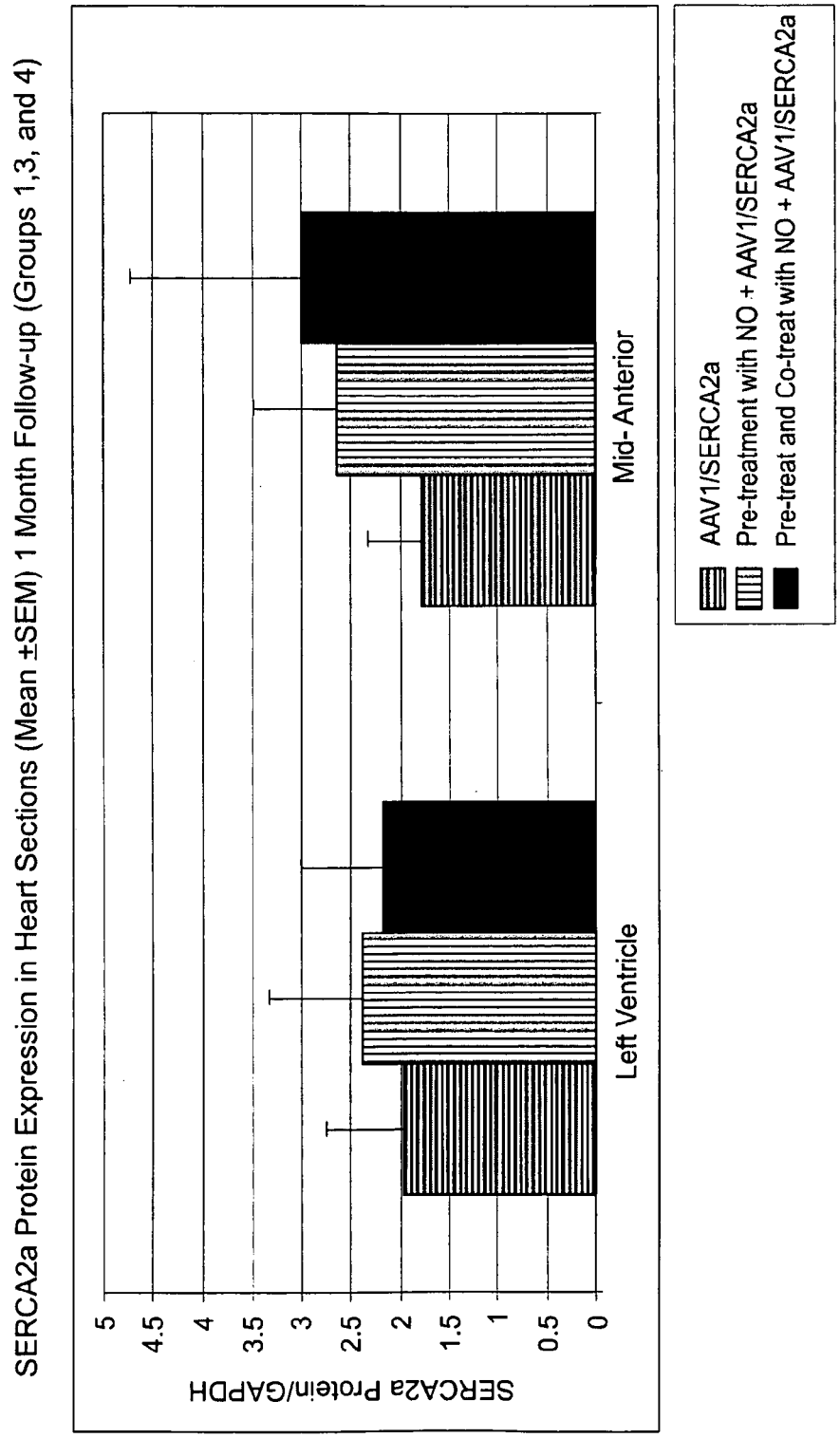
FIG. 3. Results from a 30 day, single dose, tissue distribution study of direct intracoronary infusion of AAV1/SERCA2a in normal Göttingen Minipigs. Graphs demonstrate SERCA2a protein expression in heart sections at a 1-month of follow-up from Groups 1, 2, 3 and 4.

Results show substantial improvement in one or more biological activity/efficacy measures in the subjects that were treated with AAV1/SERCA2a and nitroglycerin compared to the subjects that were treated with AAV1/SERCA2a without nitroglycerin. SERCA2a expression was assessed via RT-PCR (mRNA) and Western blot (protein) in the heart (LV free wall, LV posterior (inferior) segment, and LV anterior segment) at terminal sacrifice on Day 30 from heart sections as shown in FIG. 1 (Map of Heart Sections for Expression of SERCA2a: A (basal layer of LV): #1 septum; #2 LV anterior wall; #3 LV free wall; #4 LV posterior wall; B (middle layer of LV): #5 septum; #6 LV anterior wall; #7 LV free wall; #8 LV posterior wall; C (apical layer of LV): #9 LV anterior wall; #10 LV posterior wall; (RV): #11 RV free wall basal layer; #12 RV free wall apical layer). Total mRNA and protein expression in the left ventricle of individual sections was calculated (sum of sections 1-10 in FIG. 1), and the septum (section #5 in FIG. 1), and the middle layer anterior wall (section #6 in FIG. 1) were also analyzed separately, as these regions represent deep myocardium, furthest from the site of infusion. Obtaining adequate gene transfer into these deep myocardial regions is most difficult; however, administration of nitroglycerin enhanced vector uptake, especially in these territories. The results below show improvement in expression of SERCA2a mRNA and protein when AAV1/SERCA2a was administered in combination with nitroglycerin, especially in the LV Mid-Anterior wall and Septum, see FIGS. 2, and 3, respectively. The increase of mRNA and protein shown in these figures are in addition to the normal background levels of SERCA2a mRNA and protein. This is in contrast to humans suffering from cardiac failure, wherein SERCA2a expression levels are below normal levels. Thus, it is expected that the affect of AAV1/SERCA2a treatment on SERCA2a expression levels in patients with cardiac failure will be even more pronounced than the effect reported in FIGS. 2 and 3, given the lower baseline level of SERCA2a expression.

Safety

Figure 4:
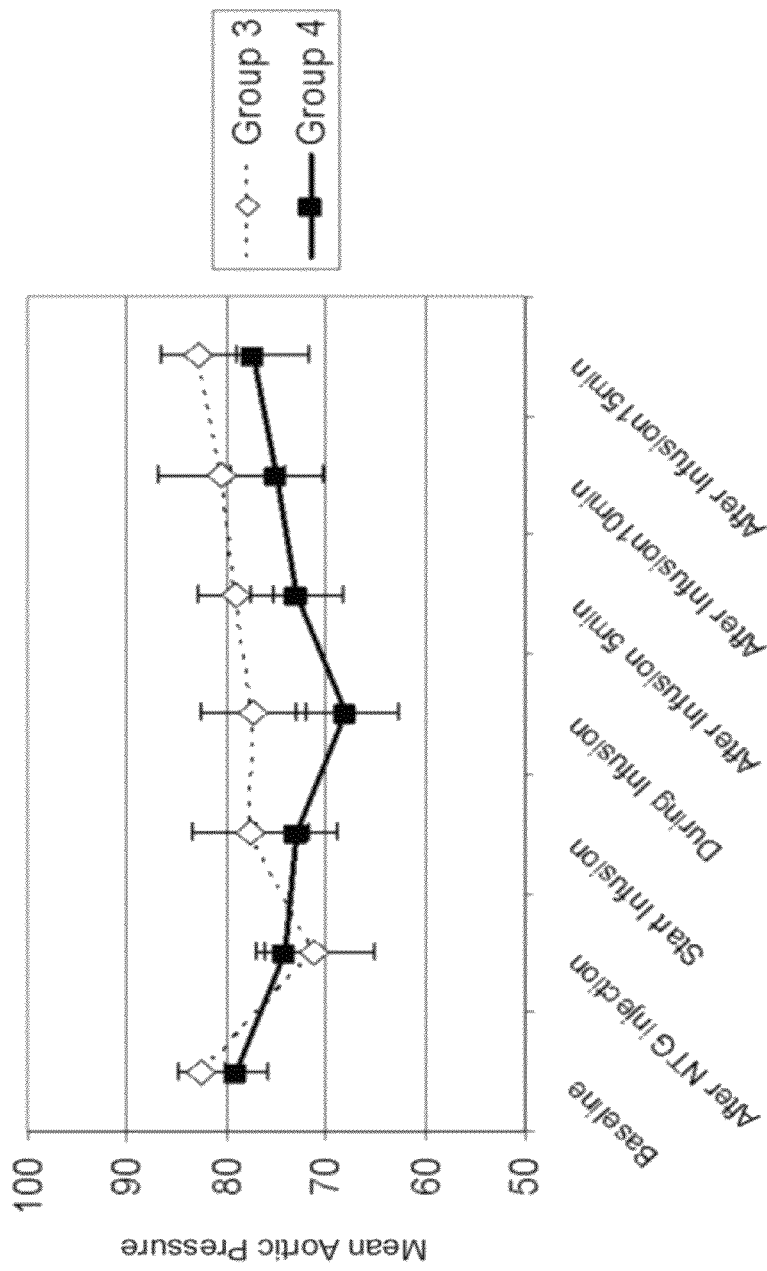
FIG. 4. The mean aortic pressures from Groups 3 and 4 during experimental procedure for the administration of AAV1/SERCA2a in normal Göttingen Minipigs.

The mean aortic pressures from Groups 3 and 4 are shown in FIG. 4. The changes seen are for the most part within what would be expected over the course of an experiment. Note that there was a maximum of 6 mm Hg decrease in Mean arterial pressure (MAP) compared to baseline and except for one time point in group 4, all other changes for nitroglycerin treated animals were within that same range. A modest decrease in MAP such as this is not meaningful and poses no safety concern. By comparison, Sasano et al. reported a decrease in blood pressure of 30 mmHg after infusion of the pretreatment and virus solutions. Moreover, subjects in the Sasano study experienced a decrease in heart rate that averaged about 50-60/minute. Authors report that the blood pressure and heart rate stabilized within the first minute of perfusion. Nevertheless, ventricular fibrillation (VF) occurred during coronary infusion at a 50% rate for the first 10 pigs but dropped to 5.6% for the remaining 71 pigs.

EXAMPLE 2

Preliminary Phase I Clinical Results—Effect of Nitroglycerin on Endpoint Measure of Cardiac Function in Patients Receiving MYDICAR®

| Protocol Synopsis | |
|---|---|
| Protocol Number: | CELL-001 |
| Title: | A Phase 1 Trial of Intracoronary Administration of MYDICAR ® (AAV1/SERCA2a) in Subjects with Heart Failure Divided into Two Stages: Stage One—Open-Label, Sequential Dose-Escalation Cohorts Followed in Stage Two—by Randomized, Double-Blind, Placebo-Control, Parallel Cohorts |
| Short Title: | Calcium Up-Regulation by Percutaneous Administration of Gene therapy In Cardiac Disease (CUPID Trial) |
| Development Phase: | 1 |
| Objectives: | To demonstrate the safety and feasibility of a single antegrade epicardial coronary artery infusion of 4 dose levels of AAV1 vector expressing the transgene for SERCA2a to subjects with ischemic or non-ischemic cardiomyopathy and NYHA Class III/IV symptoms of heart failure To demonstrate the activity/efficacy of MYDICAR ® in order to validate appropriate dose levels for future studies |
| Study Design: | This is a phase 1, multi-center, two-stage trial of a single intracoronary administration of AAV1/SERCA2a (MYDICAR ®). In Stage 1, 12 subjects, 3 subjects each in 4 sequential dose escalation cohorts, will be enrolled and treated with open-label MYDICAR ®. The rate of enrolling and treating subjects will be controlled as follows: Within Cohorts 1 and 2, a subject will be observed for a minimum of 1 week before treating the next subject in that cohort. For Cohorts 3 and 4, the first subject will be observed for a minimum of 6 weeks before treating the second subject, and the second subject will be observed for a minimum of 1 week before treating the third subject. In order to advance to the next cohort, 2 of the 3 subjects will be observed for a minimum of 90 days and the third subject for a minimum of 30 days and their safety data reviewed by the Data Monitoring Committee (DMC). After all subjects in Stage 1 are enrolled and 2 of the 3 subjects in the fourth cohort have been observed for a minimum of 90 days and the third subject for a minimum of 30 days, the DMC will review all safety data available at that time and make recommendations for opening Stage 2 of the trial. An additional 33 or 34 subjects may be enrolled in Stage 2 of the trial in a double-blinded, parallel cohort design. Subjects will be treated with one of 2 or 3 doses of MYDICAR ® or placebo. The dose groups will be recommended by the DMC based on an assessment of all safety and efficacy data available from Stage 1 subjects at that time. If 3 doses are recommended, subjects will be randomized in a ratio of 8:8:8:9 (MYDICAR ®:MYDICAR ®:MYDICAR ®:placebo). If 2 doses are recommended, subjects will be randomized in a ratio of 11:11:12 (MYDICAR ®:MYDICAR ®:placebo). All subjects in Stages 1 and 2 will be seen at screening over 2 visits, Day 0 for investigational product administration followed by continuous observation in the hospital for 18-24 hours post-dose; at weeks 1, 2, 3, 4, 5 and 6; and at months 2, 3, 6, 9 and 12. All subjects will then undergo long-term follow-up via semi-structured telephone questionnaires every 6 months for an additional 2 years. |
| Number of Subjects: | A total of 34 to 36 subjects will be treated with MYDICAR ® with or without nitroglycerin, and 9 to 12 subjects will be treated with placebo with or without nitroglycerin. In Stage 1, 12 subjects will be treated with open-label MYDICAR ® with or without nitroglycerin. In Stage 2, 24 subjects will be randomized to MYDICAR ® with or without nitroglycerin and 9 subjects will be randomized to placebo with or without nitroglycerin if 3 doses of MYDICAR ® are evaluated, or 22 subjects will be randomized to MYDICAR ® with or without nitroglycerin and 12 subjects will be randomized to placebo with or without nitroglycerin if 2 doses of MYDICAR ® are studied. |
| Method of Subject Assignment: | In Stage 1, all subjects will be assigned open-label MYDICAR ® with or without nitroglycerin in all 4 cohorts. In Stage 2, subjects will be randomized centrally in a ratio of 8:8:8:9 (MYDICAR ®:MYDICAR ®:MYDICAR ®:placebo, all with or without nitroglycerin) if 3 doses MYDICAR ™ are selected or in a ratio of 11:11:12 (MYDICAR ®:MYDICAR ®:placebo, all with or without nitroglycerin) if 2 doses of MYDICAR ® are selected. |
| No. of Study Centers: | Up to 9 centers in the United States |
| Diagnosis: | Adult subjects with NYHA Class III/IV chronic heart failure due to ischemic or non-ischemic cardiomyopathy |

| | Protocol Synopsis |
|---|---|
| Inclusion Criteria: | Screening should be performed within 30 days prior to administration of MYDICAR ® or placebo on Day 0.<br>1. Age 18-75 years of age<br>2. Chronic ischemic or non-ischemic cardiomyopathy. Subjects with ischemic cardiomyopathy should have at least one major coronary vessel with TIMI grade 3 flow.<br>3. Left ventricular ejection fraction (LVEF) $\leq$30%<br>4. Diagnosis of NYHA Class III/IV heart failure for a minimum of 6 months prior to enrollment<br>5. Maximal oxygen consumption (VO$_2$ max) $\leq$16 mL/kg/min within 90 days prior to enrollment<br>6. An implantable cardioverter defibrillator (ICD) implanted a minimum of 30 days prior to enrollment<br>7. Treatment with appropriate heart failure therapy as tolerated, including, but not limited to:<br>a. Medical therapy as tolerated, including angiotensin receptor blocker and/or angiotensin receptor converting enzyme inhibitor, beta blocker and aldosterone antagonist. Dosing of the above medications should be stable for a minimum of 30 days prior to enrollment; and/or<br>b. Resynchronization therapy, if clinically indicated, should have been implanted at least 6 months prior to enrollment<br>8. All women of childbearing potential should have a negative urine pregnancy test prior to administration of investigational product and agree to use adequate contraception (defined as oral or injectable contraceptives, intrauterine devices, surgical sterilization or a combination of a condom and spermicide) or limit sexual activity to vasectomized partner for 3 months after administration of investigational product. Men capable of fathering a child should agree to use barrier contraception (combination of a condom and spermicide) or limit activity to post-menopausal, surgically sterilized, or a contraception-practicing partner, for 3 months after administration of investigational product.<br>9. Ability to sign Informed Consent Form (ICF) and Release of Medical Information Form |
| Exclusion Criteria: | 1. Any intravenous therapy with positive inotropes, vasodilators, or diuretics within 30 days prior to enrollment<br>2. Restrictive cardiomyopathy, obstructive cardiomyopathy, pericardial disease, amyloidosis, infiltrative cardiomyopathy, uncorrected thyroid disease, or dyskinetic LV aneurysm<br>3. Cardiac surgery, percutaneous coronary intervention, or valvuloplasty within 30 days prior to enrollment<br>4. Clinically significant myocardial infarction (e.g., ST elevation MI [STEMI] or large non-STEMI) within 6 months prior to enrollment<br>5. Prior heart transplantation, left ventricular reduction surgery (LVRS), cardiomyoplasty, passive restraint device (e.g., CorCap ™ Cardiac Support Device), surgically implanted LVAD or cardiac shunt<br>6. Likely to receive cardiac resynchronization therapy, cardiomyoplasty, LVRS, heart transplant, conventional revascularization procedure, or valvular repair within 6 months following enrollment<br>7. Prior coronary artery bypass graft(s) (CABG)<br>8. Exercise capacity primarily limited by obesity, peripheral vascular disease, or orthopedic problems and not by underlying heart failure<br>9. Known hypersensitivity to octafluoropropane (component of the intravenous echocardiography contrast agent, DEFINITY ®) or other contrast dyes used for angiography; history of, or likely need for, high dose steroid pretreatment prior to contrast angiography<br>10. Significant left main or ostial right coronary lumenal stenosis in the opinion of the investigator<br>11. Expected survival <1 year in the investigator's medical opinion<br>12. Suspected or active viral, bacterial, fungal, or parasitic infection within 48 hours prior to enrollment<br>13. Liver function tests (ALT, AST, alkaline phosphatase) >2x Upper Limit of Normal (ULN) within 30 days prior to enrollment or known intrinsic liver disease (e.g., cirrhosis, chronic hepatitis B or hepatitis C virus infection)<br>14. Current or likely need for hemodialysis within 12 months following enrollment<br>15. Bleeding diathesis or thrombocytopenia defined as platelet count <50,000 platelets/µL<br>16. Anemia defined as hemoglobin <10 g/dL<br>17. Known AIDS or HIV-positive status, or a previous diagnosis of immunodeficiency with an absolute neutrophil count <1000 cells/mm$^3$<br>18. Previous participation in a study of gene transfer<br>19. Presence of neutralizing anti-AAV1 antibodies at titer $\geq$1:4 within 6 months of screening<br>20. Receiving investigational intervention or participating in another clinical study within 30 days or within 5 half-lives of the investigational drug administration prior to enrollment<br>21. Pregnancy or lactation<br>22. Recent history of psychiatric disease (including drug or alcohol abuse) that |

| | Protocol Synopsis |
|---|---|
| | is likely to impair subject's ability to comply with protocol-mandated procedures, in the opinion of the investigator |
| Test Product: | MYDICAR ® (AAV1/SERCA2a) or matching placebo, all with or without nitroglycerin. |
| Dose: | Single Administration of MYDICAR ®: $1.4 \times 10^{11}$ DNase Resistant Particles (DRP) AAV1/SERCA2a (~$2 \times 10^9$ DRP/kg*) $6 \times 10^{11}$ DRP AAV1/SERCA2a (~$8.6 \times 10^9$ DRP/kg*) $3 \times 10^{12}$ DRP AAV1/SERCA2a (~$4.3 \times 10^{10}$ DRP/kg*) $1 \times 10^{13}$ DRP AAV1/SERCA2a (~$1.4 \times 10^{11}$ DRP/kg*) Matching placebo * Assuming a 70 kg individual Some subjects to receive 150 µg (total dose) of nitroglycerin. |
| Mode of Administration: | MYDICAR ®: Antegrade epicardial coronary artery infusion into left coronary artery and/or right coronary artery via percutaneous catheter over 10 minutes. Nitroglycerin: Antegrade epicardial coronary artery infusion into left coronary artery and/or right coronary artery via percutaneous catheter over a period of less than one minute using 1.5 cc of a 100 µg/mL solution of nitroglycerin, just prior to administration of MYDICAR ®. Alternatively, nitroglycerin was given PO + IV where PO administration was given at 0.4 mg before MYDICAR ® administration and by IV at 20 µg/minute up to 691.3 µg before and during MYDICAR ® administration. Nitroglycerin was also given in an IV regimen at 20 µg/minute up to 2118 µg before and during MYDICAR ® administration. IV nitroglycerin was terminated after administration of MYDICAR ®. No other vasodilators/permeability enhancers are administered. |
| Duration of Treatment: | Treatment consists of a single dose administration of MYDICAR ® with or without nitroglycerin or placebo with or without nitroglycerin followed by 12 months of observation. After completion of the 12 months, subjects will receive a follow-up telephone call every 6 months for an additional 2 years to elicit information about hospitalizations, new medical conditions, heart failure status, and long term survival. |
| Safety Assessments: | Physical examination Follow-up history: interim illnesses, number of days hospitalized, and adverse events Complete blood count: WBC and differential, hemoglobin, hematocrit, platelet count Blood chemistries: electrolytes, blood urea nitrogen, creatinine, total bilirubin, alkaline phosphatase, alanine aminotransferase, aspartate aminotransferase, albumin, and lactate dehydrogenase Urinalysis Creatine kinase-MB, troponin T ELISPOT (an experimental immunologic function assay) Echocardiogram Interrogation of ICD ECG |
| Primary Activity/ Efficacy Assessments: | Echocardiographic assessments (including contrast echocardiography) including LVEF, LV dimensions, regional wall motion, diastolic function, and mitral regurgitation $VO_2$ max measured during cardiopulmonary exercise testing 6-minute walk test N-terminal prohormone brain natriuretic peptide (NT-proBNP) NYHA classification Minnesota Living with Heart Failure Questionnaire (MLWHFQ) |
| Safety Oversight: | DMC Morbidity & Mortality Committee |
| Primary Endpoint: | The primary endpoint is safety as measured by the incidence and severity of adverse events, including all-cause mortality, progression of heart failure (HF) leading to hospitalization, and/or IV inotrope, vasodilator, and/or diuretics administration. The percentage of subjects experiencing an event will be calculated for survivors and for all subjects enrolled. Frequency of all-cause hospitalizations and cardiovascular hospitalizations during the 12 months following intervention will also be analyzed. The total length of stay (hospital days) will be tabulated. All deaths and hospitalizations will be classified by the blinded independent Morbidity & Mortality Committee, distinguishing between the primary cause and immediate underlying cause of death or hospitalization. Details including the date of death, immediate cause of death, underlying cause of death, notation of autopsy being performed, and clinical narrative of the event will be reported to the Sponsor as soon as feasible. The primary activity/efficacy endpoints to be evaluated and compared within and between treatment groups based on changes from baseline to 3, 6, 9 and 12 months following investigational product administration include the following: $VO_2$ max assessed by cardiopulmonary exercise testing Distance walked during the 6-minute walk test Echocardiographic assessments including left ventricular ejection fraction, LV dimensions, regional wall motion, diastolic function, and mitral regurgitation NT-proBNP level NYHA Classification |

|  | Protocol Synopsis |
| --- | --- |
| Statistical Methods: | Quality of Life assessed by Minnesota Living with Heart Failure Questionnaire (MLWHFQ)<br>In addition, echo measurements will be analyzed at one month. Safety analyses will be performed for all subjects enrolled in the study and administered the test article. Primary efficacy analysis will be performed for stage 2 subjects. Additional analyses will be performed for stage 1 and 2 subjects combined according to the respective dose levels.<br>The two principal aims of the study, in addition to demonstrating feasibility, are to demonstrate the safety of MYDICAR ® administration, validate the preliminary estimate of clinical activity, and verify appropriate dose levels for future studies of MYDICAR ®.<br>Safety will be demonstrated based on the incidence of adverse events.<br>Stage 1 study data will be analyzed descriptively. Primary efficacy analysis will be performed using Stage 2 data at 6 months after test article administration. Secondary analysis based on the 3- and 12-month data and additional analysis based on the combined data for Stage 1 and Stage 2 subjects who were administered the same dose will be performed.<br>Activity will be measured by a set of pre-specified endpoints including $VO_2$ max, LV function measured by echocardiography, 6-minute walk test, NYHA classification, NT-proBNP level and MLWHFQ. Treatment success will be evaluated based on the trends in between-group comparisons for 5 efficacy domains:<br>1. LV function and remodeling (Ejection Fraction, End Systolic Volume, other echocardiography parameters)<br>2. Symptomatic (NYHA, MLWHFQ)<br>3. Functional (6-minute walk test, $VO_2$ max)<br>4. Biomarkers (NT-proBNP)<br>5. Clinical outcome (all-cause deaths, HF hospitalizations or emergency room visits, IV inotropes/vasodilators/diuretics due to HF progression)<br>Numerical and graphical summary measures (including mean, median, standard deviation, range, histograms, and scatterplots, etc.) will be used to describe these endpoints in each treatment group at baseline, and at 1, 3, 6, 9 and 12 months post-enrollment. Mixed effects models will be used to estimate changes in each endpoint over time within each treatment group, and to estimate the difference in changes over time between treatment groups. Percent change from baseline to each time point in continuous variables will be analyzed descriptively. Both point estimates and 95% confidence intervals will be computed. Proportions of patients categorized as "improved", "no change" and "worsened" based on activity parameters observed at 1, 3, 6, and 12 months will be compared across treatment groups. |

Results

Table 2 below shows the preliminary results of this study. These results demonstrate a substantial and significant improvement in one or more activity/efficacy endpoints in the subjects that were treated with MYDICAR® and nitroglycerin compared to the subjects that were treated with MYDICAR® without nitroglycerin. For other details, see Hajjar et al., Journal of Cardiac Failure, 2008 14(5); 355-67, incorporated herein by reference in its entirety.

TABLE 2

|  | Nitroglycerin Prior To Infusion | | | Absolute Ejection Fraction (EF) (%) | | | | |
| --- | --- | --- | --- | --- | --- | --- | --- | --- |
|  | LCA, IC, µg | RCA, IC, µg | Other | Baseline | 2 Mo | 6 Mo | EF Change at 6 mo | EF Change/ Patient Status |
| Subject 1 w/o NO | — | — | — | 18 | 19 | 16 | −2 | Worsened/ (Heart Transplant >6 mo) |
| Subject 4 w/o NO | — | — | — | 16 | 13 | — | −3 | Worsened/ (Died >3 mo) |
| Subject 3 with NO | — | 150 | — | 30 | 29 | 33 | +3 | Improved/ Improved |
| Subject 2 with NO | — | — | 20 µg/min IV, 2118 µg total | 25 | 32 | 31 | +6 | Improved/ Improved |
| Subject 5 with NO | — | — | 20 µg/min IV, 691 µg total + 0.4 mg PO | 20 | 20 | 21 | +1 | Slight Improvement/ Improved |
| Subject 6 w/o NO | — | — | — | 25 | 24 | 26 | +1 | Slight Improvement/ Improved |

What is claimed is:

1. A method of treating a cardiovascular disease by transfecting cardiac cells of a large mammal, the method comprising:
   identifying a mammal in need of treatment of a cardiovascular disease;
   administering a vasodilating substance to said mammal sufficient to dilate a blood vessel of the coronary circulation; and
   administering a therapeutic polynucleotide into a lumen of a blood vessel of the coronary circulation in vivo;
   wherein said therapeutic polynucleotide is infused into said lumen of a blood vessel over a period of at least about three minutes, wherein the coronary circulation is not isolated or substantially isolated from the systemic circulation of the mammal, and wherein said therapeutic polynucleotide transfects cardiac cells of said mammal resulting in the treatment of said cardiovascular disease.

2. The method of claim 1, wherein said vasodilating substance is a nitric oxide (NO) increasing substance.

3. The method of claim 2, wherein said NO increasing substance is nitroglycerin.

4. The method of claim 2, wherein said NO increasing substance is administered into a blood vessel of the coronary circulation.

5. The method of claim 4, wherein said NO increasing substance is administered in a manner selected from the group consisting of: prior to said infusion of said therapeutic polynucleotide, concurrently with said infusion of said therapeutic polynucleotide, and prior to and concurrently with said infusion of said therapeutic polynucleotide.

6. The method of claim 4, wherein said NO increasing substance is administered as a bolus injection prior to said infusion of said therapeutic polynucleotide, and said vasodilating substance is not administered more than 5 minutes prior to said infusion of said therapeutic polynucleotide.

7. The method of claim 4, wherein said NO increasing substance is administered as a bolus injection prior to said infusion of said therapeutic polynucleotide, said vasodilating substance is not administered more than 5 minutes prior to said infusion of said therapeutic polynucleotide, and wherein said NO increasing substance is infused into said blood vessel concurrently with said infusion of said therapeutic polynucleotide over a period of at least about 10 minutes.

8. The method of claim 4, wherein the NO increasing substance is about 50 µg to about 150 µg of nitroglycerin.

9. The method of claim 4, wherein said administration of said NO increasing substance comprises antegrade epicardial coronary artery injection of 1.5 mL of a 100 µg/mL solution of nitroglycerin into at least one of a left or right coronary artery via percutaneous catheter over a period of less than 1 minute, prior to said infusion of said therapeutic polynucleotide, and wherein no other vasodilator or vascular permeation enhancer other than nitroglycerin is administered to said mammal.

10. The method of claim 9, further comprising infusing nitroglycerin into said blood vessel concurrently with said infusion of said therapeutic polynucleotide.

11. The method of claim 9, wherein said mammal is a human and said cardiovascular disease is heart failure, wherein said therapeutic polynucleotide is packaged in a DNAse resistant particle (DRP) of a AAV2/1 viral vector, and a total number of DRP infused into said lumen of a blood vessel is not more than about $1\times10^{13}$, wherein the therapeutic polynucleotide comprises a SERCA2a coding sequence, wherein said blood vessel is at least one of the left or right coronary artery, and wherein said infusion of said therapeutic polynucleotide lasts at least about 10 minutes.

12. The method of claim 11, wherein said treatment improves a measurement of absolute ejection fraction of said human's heart six months after said treatment as compared to a measurement of absolute ejection fraction of said human's heart prior to said treatment.

13. The method of claim 2, wherein said NO increasing substance is administered systemically.

14. The method of claim 13, wherein said NO increasing substance is administered systemically in a manner selected from the group consisting of: intravenous injection, intravenous infusion, oral administration, transdermal administration, and subcutaneous administration.

15. The method of claim 14, wherein said NO increasing substance is administered in a manner selected from the group consisting of: prior to said infusion of said therapeutic polynucleotide, concurrently with said infusion of said therapeutic polynucleotide, and prior to and concurrently with said infusion of said therapeutic polynucleotide.

16. The method of claim 13, wherein said NO increasing substance is nitroglycerin.

17. The method of claim 16, wherein about 0.1 mg to about 2.5 mg of nitroglycerin is administered by intravenous infusion over a period of at least 10 minutes, prior to said infusion of said therapeutic polynucleotide, and wherein no other vasodilator or vascular permeation enhancer other than nitroglycerin is administered to said mammal.

18. The method of claim 17, further comprising infusing an additional amount of nitroglycerin concurrently with said infusion of said therapeutic polynucleotide.

19. The method of claim 17, wherein said mammal is a human and said cardiovascular disease is heart failure, wherein said therapeutic polynucleotide is packaged in a DNAse resistant particle (DRP) of a AAV2/1 viral vector, and a total number of DRP infused into said lumen of a blood vessel is not more than about $1\times10^{13}$, wherein the therapeutic polynucleotide comprises a SERCA2a coding sequence, wherein said blood vessel is at least one of the left or right coronary artery, and wherein said infusion of said therapeutic polynucleotide lasts at least about 10 minutes.

20. The method of claim 19, wherein said treatment improves a measurement of absolute ejection fraction of said human's heart six months after said treatment as compared to a measurement of absolute ejection fraction of said human's heart prior to said treatment.

21. The method of claim 9, wherein said infusion of said therapeutic polynucleotide begins not more than three minutes after completion of said injection of nitroglycerin prior to said infusion of said therapeutic polynucleotide.

22. The method of claim 17, wherein said infusion of said therapeutic polynucleotide begins not more than three minutes after completion of said period of intravenous infusion of nitroglycerin prior to said infusion of said therapeutic polynucleotide.

23. The method of claim 3, wherein said NO increasing substance is administered prior to and concurrently with said infusion of said therapeutic polynucleotide.

* * * * *

UNITED STATES PATENT AND TRADEMARK OFFICE
CERTIFICATE OF CORRECTION

| | | |
|---|---|---|
| PATENT NO. | : 8,221,738 B2 | Page 1 of 1 |
| APPLICATION NO. | : 12/260953 | |
| DATED | : July 17, 2012 | |
| INVENTOR(S) | : Zsebo | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this
Seventh Day of October, 2014

Michelle K. Lee
*Deputy Director of the United States Patent and Trademark Office*